US011844872B2

(12) United States Patent
Michalakos et al.

(10) Patent No.: US 11,844,872 B2
(45) Date of Patent: Dec. 19, 2023

(54) MOBILE SANITIZATION SYSTEMS AND METHODS

(71) Applicant: HONEYWELL INTERNATIONAL INC., Charlotte, NC (US)

(72) Inventors: Peter Michalakos, Des Plaines, IL (US); Giorgio Isella, Torrance, CA (US); Brian Wenig, Phoenix, AZ (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 303 days.

(21) Appl. No.: 17/150,706

(22) Filed: Jan. 15, 2021

(65) Prior Publication Data

US 2022/0226525 A1 Jul. 21, 2022

(51) Int. Cl.
*A61L 2/24* (2006.01)
*A61L 2/10* (2006.01)
*A61L 2/22* (2006.01)

(52) U.S. Cl.
CPC .................. *A61L 2/24* (2013.01); *A61L 2/10* (2013.01); *A61L 2/22* (2013.01); *A61L 2202/11* (2013.01); *A61L 2202/14* (2013.01); *A61L 2202/15* (2013.01); *A61L 2202/16* (2013.01)

(58) Field of Classification Search
CPC ..... A61L 2/10; A61L 2202/11; A61L 2202/16
See application file for complete search history.

(56) References Cited

U.S. PATENT DOCUMENTS

| 5,383,605 | A | * | 1/1995 | Teague | .................... B60S 3/044 239/525 |
| 8,907,304 | B2 | * | 12/2014 | Kreitenberg | .............. A61L 2/10 250/492.1 |
| 9,144,618 | B2 | | 9/2015 | Kreitenberg | |

(Continued)

FOREIGN PATENT DOCUMENTS

| CN | 205108454 U | 3/2016 |
| CN | 205867147 U | 1/2017 |

(Continued)

OTHER PUBLICATIONS

Xinhengjia Security Robots & Others, "Sterilization Robot XT-A," Jul. 15, 2020, downloaded from https://www.xinhengjiarobotics.com/xta1gclid=CjwKCAjwr7X4BRA4EiwAUXjbt_9IWiwbEfSkLdSID30lcm1gM5r9fxivDO0bLIocwu6ntQHwuYCqPBoC . . . .

*Primary Examiner* — Sean E Conley
*Assistant Examiner* — Justin Hwang
(74) *Attorney, Agent, or Firm* — LORENZ & KOPF, LLP

(57) ABSTRACT

A mobile sanitization system includes a movable trolley having an arm that is extendable between a first position in which the arm is in a collapsed state and a second position in which the arm is extended outwardly. The mobile sanitization system includes at least one ultraviolet light source coupled to the arm that is configured to illuminate to disinfect. The mobile sanitization system includes a source of liquid disinfectant and at least one nozzle fluidly coupled to the source of liquid disinfectant. The nozzle is coupled to at least one of the trolley and the arm, and the nozzle is (Continued)

configured to dispense the liquid disinfectant. The mobile sanitization system includes a spray wand removably coupled to the trolley and fluidly coupled to the source of liquid disinfectant. The spray wand is removable from the trolley to dispense the liquid disinfectant to disinfect a targeted area.

18 Claims, 12 Drawing Sheets

(56) References Cited

U.S. PATENT DOCUMENTS

| | | | |
|---|---|---|---|
| 9,635,848 B2* | 5/2017 | Needham | A01M 7/0089 |
| 2015/0165459 A1* | 6/2015 | Venard | B05B 9/007 |
| | | | 239/71 |
| 2016/0271803 A1* | 9/2016 | Stewart | B25J 11/0085 |
| 2017/0283092 A1 | 10/2017 | Brown et al. | |
| 2018/0369438 A1* | 12/2018 | Grossman | A61L 2/18 |

FOREIGN PATENT DOCUMENTS

| | | | | |
|---|---|---|---|---|
| CN | 107126156 A | * | 9/2017 | A47L 11/00 |
| CN | 107320022 A | | 11/2017 | |
| CN | 210185484 U | | 3/2020 | |
| KR | 20100121711 A | | 11/2010 | |
| WO | 2017034487 A2 | | 3/2017 | |
| WO | 2020060507 A1 | | 3/2020 | |
| WO | WO-2020060507 A1 | * | 3/2020 | A47L 11/00 |

* cited by examiner

MOBILE SANITIZATION SYSTEMS AND METHODS

TECHNICAL FIELD

The present disclosure generally relates to systems and methods for sanitization of one or more surfaces, and more particularly relates to systems and methods for mobile sanitization of one or more surfaces onboard a mobile platform.

BACKGROUND

Typically, one or more surfaces of common areas may require sanitizing throughout the course of use to reduce the presence of bacteria and the like on the surfaces. In the example of a mobile platform, such as a ship, bus, train, aircraft, etc., a system for sanitizing the mobile platform may need to be portable or mobile to be used in between routes traveled by the mobile platform. In addition, in the example of a mobile platform, the cleaning of surfaces of common areas may be difficult due to the configuration of the passenger seating onboard the mobile platform. For example, certain areas, such as beneath passenger seats, luggage stowage compartment handles, etc. may be hard to reach by an operator for cleaning. In addition, in certain instances, it may be desirable to disinfect the surfaces of common areas using one or more disinfection techniques to ensure a desired level of sanitization.

Accordingly, it is desirable to provide mobile sanitization systems and methods that enable an operator to easily disinfect all surfaces of the mobile platform. In addition, it is desirable to provide systems ad method for mobile sanitization that enable an operator to disinfect surfaces using one or more disinfection techniques. Furthermore, other desirable features and characteristics of the present invention will become apparent from the subsequent detailed description and the appended claims, taken in conjunction with the accompanying drawings and the foregoing technical field and background.

SUMMARY

According to various embodiments, provided is a mobile sanitization system. The mobile sanitization system includes a movable trolley having an arm that is extendable from a first position in which the arm is in a collapsed state within the trolley and a second position in which the arm is extended outwardly from the trolley. The mobile sanitization system includes at least one ultraviolet light source coupled to the arm, and the at least one ultraviolet light source is configured to illuminate to disinfect at least one surface. The mobile sanitization system includes at least one source of liquid disinfectant coupled to the trolley. The mobile sanitization system includes at least one nozzle fluidly coupled to the at least one source of liquid disinfectant. The at least one nozzle is coupled to at least one of the trolley and the arm, and the at least one nozzle is configured to dispense the liquid disinfectant to disinfect the at least one surface. The mobile sanitization system includes a spray wand removably coupled to the trolley and fluidly coupled to the at least one source of liquid disinfectant. The spray wand is configured to be removed from the trolley to dispense the liquid disinfectant to disinfect a targeted area of the at least one surface.

The trolley has a first end opposite a second end, the arm is coupled proximate the first end, and the at least one nozzle is coupled to the trolley proximate the second end. The at least one nozzle includes at least one nozzle coupled to each of the trolley and to the arm, and the mobile sanitization system further includes a valve coupled between the at least one source of liquid disinfectant and the at least one nozzle coupled to each of the trolley and to the arm. The valve is responsive to one or more control signals to move between an opened position to enable the liquid disinfectant to flow to the at least one nozzle and a closed position. The mobile sanitization system includes a controller, having a processor, configured to: output one or more control signals to the valve to move the valve to the opened position or the closed position based on a condition associated with the mobile sanitization system. The condition is an interlock condition. The controller is configured to receive interlock data from an interlock sensor and determine whether the condition is satisfied based on the interlock data. The controller is configured to output the one or more control signals to the valve based on the interlock condition being satisfied. The trolley includes a propulsion system configured to move the trolley and based on the interlock condition as unsatisfied, the controller outputs one or more control signals to the propulsion system to halt a movement of the trolley. The mobile sanitization system includes a source of speed data associated with a speed of the motion of the trolley, and the at least one ultraviolet light source is configured to illuminate based on the speed data. The at least one ultraviolet light source is responsive to one or more control signals from the controller to illuminate, and the controller outputs the one or more control signals based on whether the spray wand is removed from the trolley. The mobile sanitization system includes a communication system, and the controller is configured to determine an amount of liquid disinfectant dispensed by the at least one nozzle coupled to each of the trolley and to the arm and to output the dosage to a remote entity via the communication system. The mobile sanitization system includes a source of speed data associated with a speed of the motion of the trolley and a pump configured to supply the at least one nozzle with the liquid disinfectant, and a flow rate of the pump is based on the speed data. The trolley includes at least one handle, and an interlock sensor is associated with the at least one handle.

Further provided is a mobile sanitization system. The mobile sanitization system includes a movable trolley having an arm that is extendable from a first position in which the arm is in a collapsed state within the trolley and a second position in which the arm is extended outwardly from the trolley. The mobile sanitization system includes at least one ultraviolet light source coupled to the arm, and the at least one ultraviolet light source is configured to illuminate to disinfect at least one surface. The mobile sanitization system includes at least one source of liquid disinfectant coupled to the trolley. The mobile sanitization system includes at least one trolley nozzle fluidly coupled to the at least one source of liquid disinfectant and coupled to the trolley. The at least one trolley nozzle is configured to dispense the liquid disinfectant to disinfect the at least one surface. The mobile sanitization system includes at least one arm nozzle fluidly coupled to the at least one source of liquid disinfectant and coupled to the arm. The at least one arm nozzle is configured to dispense the liquid disinfectant to disinfect the at least one surface. The mobile sanitization system includes a spray wand removably coupled to the trolley and fluidly coupled to the at least one source of liquid disinfectant. The spray wand is configured to be removed from the trolley to dispense the liquid disinfectant to disinfect a targeted area of the at least one surface.

The trolley has a first end opposite a second end, the arm is coupled proximate the first end, and the at least one trolley nozzle is coupled to the trolley proximate the second end. The at least one arm nozzle comprises a plurality of arm nozzles coupled to the arm to extend about at least a portion of a perimeter of the arm. The trolley includes at least one handle, and an interlock sensor is associated with the at least one handle.

Further provided is a method of sanitizing one or more surfaces of a mobile platform. The method includes receiving, by a processor, at least one of an input to activate at least one light source associated with a mobile sanitization system to disinfect the one or more surfaces or an input to activate at least one nozzle to dispense a liquid disinfectant associated with the mobile sanitization system to disinfect the one or more surfaces. The method includes determining, by the processor, whether an interlock condition associated with the mobile sanitization system is satisfied, and outputting, by the processor, one or more control signals to activate at least one of the at least one light source and the at least one nozzle based on the input and the interlock condition as satisfied. The method includes deactivating, by the processor, the at least one light source or the at least one nozzle based on the input and the interlock condition as unsatisfied.

The deactivating the at least one nozzle further includes outputting, by the processor, one or more control signals to a valve coupled between the at least one nozzle and a reservoir to close the valve based on the interlock condition as unsatisfied. The method includes determining, by the processor, whether an input has been received to dispense the liquid disinfectant through a spray wand associated with the mobile sanitization system based on the interlock condition. The input is to activate the at least one light source and the method includes receiving, by the processor, speed data associated with a speed of the mobile sanitization system; determining, by the processor, whether a dosage of the at least one light source meets a guideline for the mobile platform based on the speed of the mobile platform; and adjusting the output of the at least one light source based on the determining. The input is to activate the at least one nozzle and the method includes receiving, by the processor, speed data associated with a speed of the mobile sanitization system; determining, by the processor, whether a dosage of the at least one nozzle meets a guideline for the mobile platform based on the speed of the mobile platform; and adjusting the output of the at least one nozzle based on the determining.

DESCRIPTION OF THE DRAWINGS

The exemplary embodiments will hereinafter be described in conjunction with the following drawing figures, wherein like numerals denote like elements, and wherein.

DETAILED DESCRIPTION

Figure 1:
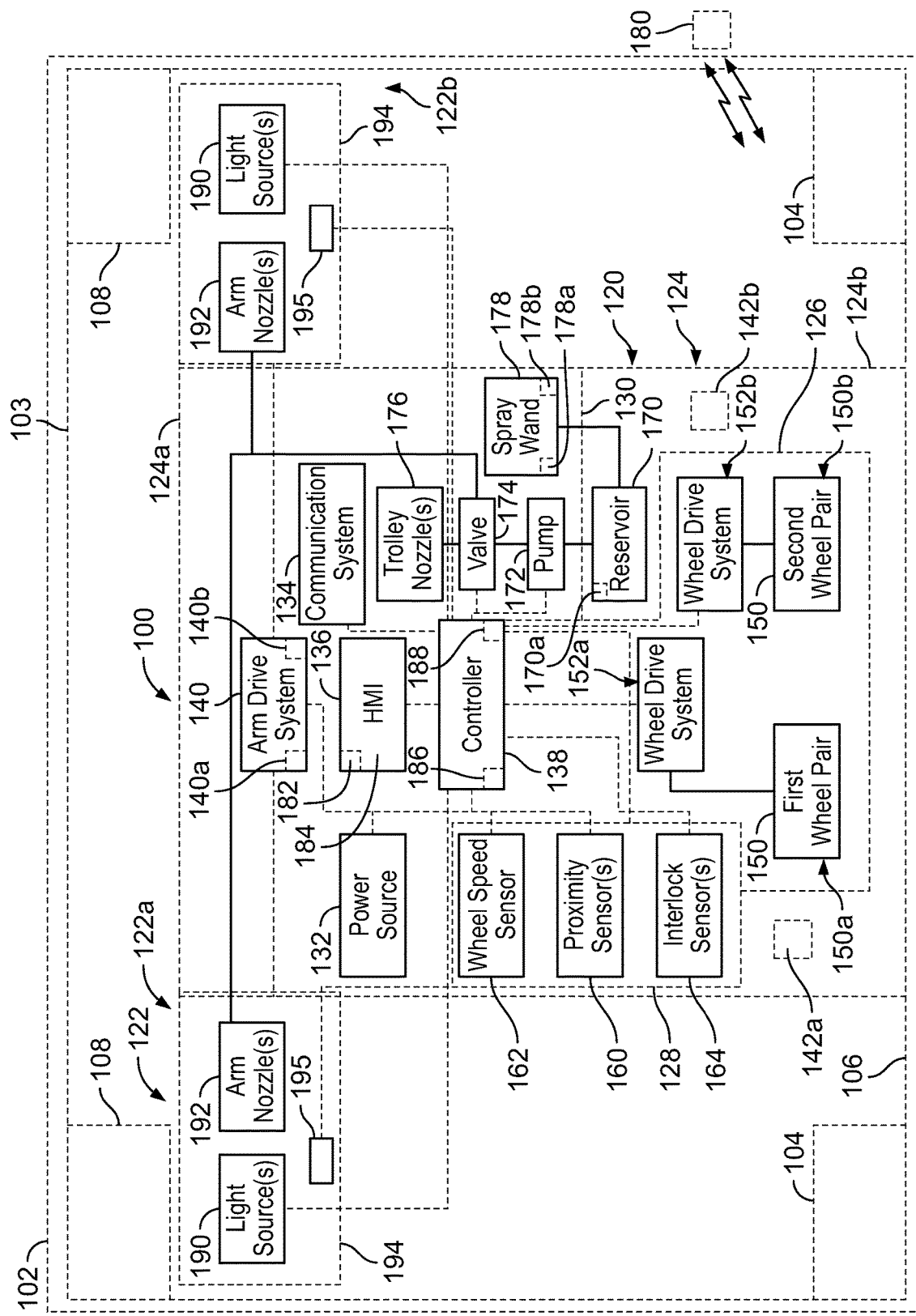
FIG. 1 is a functional block diagram of an exemplary mobile sanitization system in accordance with the various teachings of the present disclosure.

The following detailed description is merely exemplary in nature and is not intended to limit the application and uses. Furthermore, there is no intention to be bound by any expressed or implied theory presented in the preceding technical field, background, brief summary or the following detailed description. In addition, those skilled in the art will appreciate that embodiments of the present disclosure may be practiced in conjunction with any type of sanitization system that would benefit from the use of multiple disinfection techniques and the mobile sanitization system described herein is merely one exemplary embodiment according to the present disclosure. In addition, while the mobile sanitization system is described herein as being used onboard a mobile platform, such as a bus, train, motor vehicle, marine vessel, aircraft, rotorcraft and the like, the various teachings of the present disclosure can be used with on a stationary platform. Further, it should be noted that many alternative or additional functional relationships or physical connections may be present in an embodiment of the present disclosure. In addition, while the figures shown herein depict an example with certain arrangements of elements, additional intervening elements, devices, features, or components may be present in an actual embodiment. It should also be understood that the drawings are merely illustrative and may not be drawn to scale.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominantly in the respective nominal axial or radial direction. As used herein, the term "transverse" denotes an axis that crosses another axis at an angle such that the axis and the other axis are neither substantially perpendicular nor substantially parallel. As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the sanitization systems described herein are merely exemplary embodiments of the present disclosure.

For the sake of brevity, conventional techniques related to signal processing, data transmission, signaling, control, machine learning models, radar, lidar, image analysis, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

With reference to FIG. 1, a functional block diagram illustrates a mobile sanitization system 100 for use on a mobile platform 102. The mobile platform 102 may include a cabin 103 that includes one or more passenger seats 104 arranged in rows along one or more aisles 106. For example, the mobile platform 102 includes, but is not limited to, a bus, train, motor vehicle, marine vessel, aircraft, rotorcraft and the like. The mobile sanitization system 100 is sized to be positionable within one of the aisles 106 and movable along the aisle 106 from a first end of the aisle 106 to an opposite second end of the aisle 106. This allows the mobile sanitization system 100 to disinfect and sanitize the surfaces of the cabin 103 along the aisle 106 including the surfaces associated with the passenger seats 104 and surfaces surrounding the passenger seats 104. In certain instances, one or more stowage compartments 108 may be positioned above each of the passenger seats 104 along the aisle 106. The stowage compartments 108 may stow luggage, personal items, mobile platform supplies, etc. The mobile sanitization system 100 may also clean surfaces associated with the stowage compartments 108 as it traverses the aisle 106, along with galleys and lavatories onboard the mobile platform 102. As will be discussed, the mobile sanitization system 100 cleans, disinfects and sanitizes one or more surfaces of the cabin 103 of the mobile platform 102 as the mobile sanitization system 100 traverses along the aisle 106 to eliminate bacteria, viruses, etc. It should be noted that in the instances of the mobile platform 102 having multiple aisles 106, the mobile sanitization system 100 may traverse each aisle to clean the respective surfaces. In addition, the mobile sanitization system 100 may clean the respective surfaces in a single pass or trip down the aisle 106, which may reduce a time needed to clean the mobile platform 102.

In one example, the mobile sanitization system 100 includes a movable trolley 120 and at least one extendable arm 122. In this example, the mobile sanitization system 100 includes two extendable arms 122a, 122b on opposed sides of the trolley 120. It should be noted, however, that the trolley 120 may include a single extendable arm, or more than two extendable arms, such as four extendable arms, for example. The trolley 120 includes a housing 124, a propulsion system 126, one or more sensors 128, a disinfectant system 130, a power source 132, a communication system 134, a human-machine interface (HMI) 136 and a controller 138. The trolley 120 may also include an arm drive system 140, which is coupled to the extendable arms 122a, 122b to move the extendable arms 122a, 122b relative to the trolley 120, as will be discussed further herein.

The housing 124 supports the extendable arms 122a, 122b on opposed sides of the housing 124. The housing 124 may be any suitable shape for traversing the aisles 106, and in one example, is generally rectangular. The housing 124 may be composed of any suitable material, including, but not limited to, metal, metal alloy, a polymer-based material, etc. In one example, the housing 124 may include an internal support structure or frame, which is enclosed by one or more panels. The panels may be composed of a material that is different than the frame. The housing 124 includes at least one graspable member or handle 142 on an exterior surface. Generally, the at least one handle 142 includes two handles 142a, 142b. The handles 142a, 142b are coupled to opposed sides of the housing 124 so as to face opposed ends of the aisle 106. It should be noted that the location of the handles 142a, 142b in FIG. 1 is merely an example, as generally, the handles 142a, 142b are positioned on the housing 124 at a location that enables the operator to grasp the respective handle 142a, 142b as the mobile sanitization system 100 traverses down the aisle 106. Each of the handles 142a, 142b may extend outwardly from the housing 124, or may be recessed within the housing 124, if desired. Each of the handles 142a, 142b is coupled to one of the one or more sensors 128, as will be discussed.

In this example, the propulsion system 126 moves or drives the trolley 120 along the aisle 106. Thus, in one example, the mobile sanitization system 100 is self-propelled. The propulsion system 126 includes at least one wheel 150 that is rotatable relative to the housing 124. Generally, the number of wheels associated with the trolley 120 may be based on a size of the housing 124. In this example, the trolley 120 includes two pairs of wheels 150a, 150b. Generally, a front and a back of the housing 124 has an associated pair of wheels 150a, 150b. Each wheel 150 of the pair of wheels 150a, 150b may be interconnected via a shaft, such that a rotation of one of the wheels 150 drives the other wheel 150 of the pair of wheels 150a, 150b. At least one wheel 150 of the pair of wheels 150a, 150b is driven by an associated wheel drive system 152a, 152b. In one example, the wheel drive system 152a, 152b is an electric motor, which is responsive to one or more control signals from the controller 138 to rotate an output shaft that drives the respective one of the wheels 150 of the pair of wheels 150a, 150b. Generally, the wheel drive system 152a is responsive to the controller 138 to drive the one wheel 150 of the pair of wheels 150a to move the trolley 120 in a first direction, such as from a start of the aisle 106 to an end of the aisle 106; and the wheel drive system 152b is responsive to the controller 138 to drive the one wheel 150 of the pair of wheels 150b to move the trolley 120 in a second direction, opposite the first direction, such as from the end of the aisle 106 to the start of the aisle 106. It should be noted that other arrangements may be used to propel the trolley 120 in an autonomous manner along the aisle 106, and that this is just one example. In addition, the one wheel 150 of the pair of wheels 150a, 150b may include a steering mechanism to assist in turning the one wheel 150, and thus, the pair of wheels 150a, 150b to aid in positioning the trolley 120 within the aisle 106. In addition, while the trolley 120 is described herein as having the pair of wheels 150a, 150b that is driven by a respective wheel drive system 152a, 152b, one of the pair of wheels 150a, 150b may be driven by a wheel drive system in both directions, if desired. Stated another way, the trolley 120 may have a single pair of driven wheels that are operable to move the trolley 120 along the aisle 106 in both directions, if desired.

The one or more sensors 128 are in communication with the controller 138 over a suitable communication architecture that supports the transfer of data and power, including, but not limited to a bus. In one example, the one or more sensors 128 include one or more proximity sensors 160, a wheel speed sensor 162 and one or more interlock sensors 164. In one example, the proximity sensors 160 determine a position of the housing 124 relative to the passenger seats 104. The proximity sensors 160 may comprise an infrared sensor, however, other distancing sensors may be employed, including, but not limited to, lidar, radar, etc. The proximity sensors 160 may be coupled to the exterior surface of the housing 124. The proximity sensors 160 observe a distance of the housing 124 relative to the passenger seats 104, and output sensor signals to the controller 138. Based on the sensor signals from the proximity sensors 160, the controller 138 determines whether the trolley 120 is aligned and centered within the aisle 106.

The wheel speed sensor 162 observes a rate of rotation of one of the wheels 150 of each of the pair of wheels 150a, 150b, and generates sensor signals based on the observation, which are communicated to the controller 138. In one example, one of the wheels 150 of each of the pair of wheels 150a, 150b includes a marking, such as a painted line, etc., and the wheel speed sensor 162 is a camera that observes the marking to determine a speed of the wheel 150 (based on a time between observations of the marking, for example). In other examples, the wheel speed sensor 162 may comprise a Hall effect sensor, which observes a toothed ring coupled to the shaft that interconnects the wheels 150 of the respective pair of wheels 150a, 150b. In yet other examples, the wheel speed sensor 162 may comprise a Hall effect sensor, which is coupled to the output shaft of the motor associated with each of the wheel drive systems 152a, 152b. Thus, generally, the wheel speed sensor 162 is any suitable sensor that directly or indirectly observes an amount of rotation of the wheel 150 driven by the wheel drive system 152a, 152b and outputs sensor signals to the controller 138.

In this example, the sensors 128 includes two of the interlock sensors 164, which are associated with a respective one of the handles 142a, 142b. In one example, the interlock sensors 164 may comprise a pressure sensor, a capacitance touch sensor, a manual switch (clamp) or the like. In one example, a respective one of the interlock sensors 164 is coupled to the handle 142a, and the other of the interlock sensors 164 is coupled to the handle 142b. The interlock sensors 164 observe whether at least one hand of an operator is positioned about or coupled to the respective handle 142a, 142b, and outputs sensor signals to the controller 138 based on the observation. For example, in the example of a pressure sensor, the interlock sensors 164 observe a pressure applied by at least one of the operator's hands on the respective one of the handles 142a, 142b and generates sensor signals for the controller 138 based on the observation. In the example of a capacitance touch sensor, the interlock sensors 164 observe a change in electrostatic capacitance produced between an electrode and at least one of the operator's hands around the respective one of the handles 142a, 142b and generates sensor signals for the controller 138 based on the observation. In the example of the manual switch, the manual switch is a manual handle or clamp that is squeezed by the user to activate the wheel drive system 152a, 152b through an electrical signal received by the controller 138 or movement of a drive cable in communication with the controller 138. Thus, generally, the interlock sensors 164 observe whether at least one of the operator's hands is coupled to one of the handles 142a, 142b of the trolley 120 and generate sensor signals based on the observation that are communicated to the controller 138. In certain examples, the interlock sensors 164 may observe whether both of the operator's hands are coupled to a respective one of the handles 142a, 142b. In other examples, the interlock sensors 164 may observe whether a single one of the operator's hands are coupled to a respective one of the handles 142a, 142b.

The disinfectant system 130 includes a reservoir 170, a pump 172, a valve 174, one or more trolley nozzles 176 and a spray wand 178. The reservoir 170 contains a disinfectant, which in this example, is a liquid disinfectant. The liquid disinfectant may include, but is not limited to solutions of chlorine dioxide, stabilized chlorine dioxide, quaternary ammonium salts, sodium chlorite, sodium hypochlorite, hypochlorous acid, hydrogen chloride, citric acid, phenolic, thymol, ethanol, isopropyl alcohol, or mixtures thereof. The reservoir 170 may have any suitable shape to contain the liquid disinfectant, and may include a level sensor 170a. The level sensor 170a may observe a level of the liquid disinfectant contained in the reservoir 170, and generate sensor signals based on the observation that are communicated to the controller 138. The level sensor 170a is in communication with the controller 138 over a suitable communication architecture that supports the transfer of data and power, including, but not limited to a bus.

The pump 172 is fluidly coupled to the reservoir 170 via one or more hoses, quick connect couplings and the like, for example, to draw the liquid disinfectant from the reservoir 170. In one example, the pump 172 is a variable displacement pump, which is responsive to one or more control signals from the controller 138 to adjust a flow rate of the pump 172 as the trolley 120 moves along the aisle 106. The pump 172 is fluidly coupled to the valve 174 and the spray wand 178 to provide the liquid disinfectant at the predetermined flow rate to the valve 174 and the spray wand 178. In one example, the flow rate of the spray wand 178 may be determined by a nozzle 178b of the spray wand 178 and a flow rate of the pump 172, and the dosage applied by the spray wand 178 may be determined by the amount of time the spray wand 178 is dispensing the liquid disinfectant. The spray wand 178 is generally intended for "spot" application, in specific, hard-to-reach areas. In certain examples, the spray wand 178 may include a separate flow meter to determine an amount of fluid dispensed by the spray wand 178, if desired. The separate flow meter is in communication with the controller 138 over a suitable communication architecture that supports the transfer of data and power, including, but not limited to a bus. The pump 172 has a predetermined initial flow rate that is factory defined or pre-set based on a standard operating speed of the trolley 120 along the aisle 106 as will be discussed.

The valve 174 is fluidly coupled between the pump 172, the trolley nozzles 176 and the arm nozzles 192 via respective hoses, quick connect couplings and the like, for example, to control a flow of the liquid disinfectant from the pump 172 to the trolley nozzles 176 and the arm nozzles 192. The valve 174 is downstream of the pump 172, and upstream from the trolley nozzles 176 and the arm nozzles 192. In one example, the valve 174 is a control valve, which is responsive to one or more signals from the controller 138 to move between a first, opened position, in which the liquid disinfectant is supplied to the trolley nozzles 176 and the arm nozzles 192; and a second, closed position in which the flow of the liquid disinfectant to the trolley nozzles 176 and the arm nozzles 192 is inhibited. In certain embodiments, the valve 174 may be controlled to move to positions between the first, opened position and the second, closed position, if desired. The valve 174 may be any suitable control valve, including, but not limited to a butterfly valve, ball valve, diaphragm valve, etc., which is in communication with the controller 138 over a suitable communication architecture that supports the transfer of data and power, including, but not limited to a bus, and is fluidly coupled to the pump 172, the trolley nozzles 176 and the arm nozzles 192. In addition, the valve 174 may include a position sensor, which provides feedback of the position of the valve 174 (first, opened position or second, closed position) to the controller 138 over the communication architecture.

The trolley nozzles 176 are coupled to the housing 124 of the trolley 120 via one or more mechanical fasteners, for example. Generally, the housing 124 includes a first, top end 124a opposite a second, bottom end 124b. In one example, the trolley nozzles 176 are coupled to the housing 124 at or near the bottom end 124b. By coupling the trolley nozzles 176 at or near the bottom end 124b of the housing 124, the trolley nozzles 176 may spray the liquid disinfectant along a floor of the aisle 106. In addition, the trolley nozzles 176 may be arranged about a perimeter or on the sides of the housing 124 such that the trolley nozzles 176 may spray the liquid disinfectant under the passenger seats 104 as the mobile sanitization system 100 moves along the aisle 106. In one example, each of the trolley nozzles 176 includes, but is not limited to, a spray nozzle, misting nozzle, fogging nozzle, electrostatic nozzle, or high-volume nozzle, either with a full cone or hollow cone pattern. Each of the trolley nozzles 176 is fluidly coupled to the valve 174 via a respective hose, fluid coupling, etc. It should be noted that a manifold may be coupled between the valve 174 and the trolley nozzles 176 to assist in directing the liquid disinfectant from the valve 174 to each of the trolley nozzles 176. In one example, the trolley 120 may include one to about four trolley nozzles 176 coupled to the housing 124 about the perimeter of the housing 124 at or near the bottom end 124b. Generally, the spray of each of the trolley nozzles 176 may be about 3 feet to about 5 feet. It should be noted, that if desired, one or more of the trolley nozzles 176 may be coupled to the housing 124 at other locations along the trolley 120. For example, trolley nozzles 176 may be coupled at or near the top end 124a to assist in cleaning the stowage compartments 108. The trolley nozzles 176 may also be coupled between the top end 124a and the bottom end 124b to assist in cleaning sides of the passenger seats 104 that line the aisle 106. In addition, the trolley nozzles 176 may be directed to the porous (carpeted) floors, especially in areas under the passenger seat 104 that may be harder to illuminate with the light sources 190. Also, in certain instances, a portion of the housing 124 of the trolley 120 may be extendable relative to a fixed portion of the trolley 120 (to raise or lower a height of the arms 122a, 122b relative to the floor of the aisle 106, for example), and one or more of the trolley nozzles 176 may be coupled to the housing 124 so as to be movable with the portion of the housing 124, if desired. Thus, in certain instances, the housing 124 may include a fixed portion and a movable portion, with an actuator that is in communication with the controller 138 to move the movable portion of the housing 124 relative to the fixed portion. The controller 138 may receive input to move the movable portion of the housing 124 relative to the fixed portion via the human-machine interface 136. The trolley nozzles 176 may have a varying flow rate due to the flow rate of the pump 172.

The spray wand 178 is fluidly coupled to the pump 172 via one or more hoses, quick connect couplings and the like, for example. The spray wand 178 may also be coupled to or retained on the housing 124 of the trolley 120 by a receptacle, U-shaped holder coupled to the housing 124 or other retaining device configured to retain the spray wand 178 such that the spray wand 178 is removable from the trolley 120 for use by the operator. The spray wand 178 may comprise any suitable spray wand, including, but not limited to, a universal sprayer wand that includes a trigger 178a that is manipulatable by an operator to dispense the liquid disinfectant through the nozzle 178b associated with the spray wand 178. In one example, the trigger 178a of the spray wand 178 is in communication with the controller 138, over a suitable communication architecture that supports the transfer of data and power, including, but not limited to a bus, such that a manipulation, such as a pulling, of the trigger 178a sends a signal to the controller 138. As will be discussed, based on the signal, the controller 138 activates the pump 172 to dispense the liquid disinfectant through the nozzle 178b. The nozzle 178b may comprise any suitable nozzle for use with a spray wand, such as a spray nozzle, stream nozzle, etc. It should be noted that the spray wand 178 is merely one example, as a spray wand associated with the trolley 120 need not be in communication with the controller 138, but rather, the pump 172 may run continuously during an operation of the mobile sanitization system 100 such that a manipulation of a trigger of the spray wand dispenses the liquid disinfectant. The spray wand 178 is removable from the trolley 120 by the operator to dispense the liquid disinfectant to disinfect a targeted area of the surfaces of the cabin 103. For example, the spray wand 178 may be used to disinfect surfaces that are not easily disinfected by one or more light sources 190, the trolley nozzles 176 and/or one or more arm nozzles 192, including, but not limited to handles of the stowage compartments 108, directly underneath the passenger seats 104, seat belt buckles, corners of galleys, corners of lavatories, etc. The spray wand 178 may alternatively include a sensor that observes a position of the trigger 178a and communicates the position of the trigger 178a to the controller 138 over the communication architecture. In this example, the controller 138 may activate the pump 172 based on the observation that the trigger 178a is in a closed position.

The power source 132 supplies power to the mobile sanitization system 100. In one example, the power source 132 is a rechargeable battery pack, which may be connected to a remote power source for charging via a wired connection. It should be noted that other power sources may be employed, and the use of a rechargeable battery is merely one example. In other examples, the power source 132 may comprise a power cord, which is capable of supplying power to the mobile sanitization system 100 via a source onboard the mobile platform 102. As a further example, the power source 132 may comprise a fuel cell coupled to the trolley 120. Generally, the power source 132 is in communication with the controller 138 via a suitable communication architecture that supports the transfer of data and power, including, but not limited to a bus.

The communication system 134 is configured to wirelessly communicate information to and from other entities 180, such as but not limited to, remote ground systems, remote servers, and/or hand-held operator devices (smartphone, smart watch, tablet, etc.) and the like. In an exemplary embodiment, the communication system 134 is a wireless communication system configured to communicate via a wireless local area network (WLAN) using IEEE 802.11 standards, Bluetooth® or by using cellular data communication. In this example, the communication system 134 comprises a Bluetooth® transceiver, a satellite transceiver, a cellular transceiver, and/or a Wi-Fi transceiver to receive messages from the other entities 180 and to transmit data to the other entities 180. The communication system 134 is in communication with the controller 138 via a suitable communication architecture that supports the transfer of data and power, including, but not limited to a bus.

The human-machine interface 136 is in communication with the controller 138 via a suitable communication architecture that supports the transfer of data and power, including, but not limited to a bus. The human-machine interface 136 may be configured in a variety of ways. In some embodiments, the human-machine interface 136 may include various switches, dials, levers, one or more buttons, a touchscreen interface 182 that may be overlaid on a display 184, a keyboard, an audible device, a microphone associated with a speech recognition system, the trigger 178a of the spray wand 178, or various other human-machine interface devices. The human-machine interface 136 is coupled to the housing 124. In certain instances, the display 184 may be removably coupled to the housing 124, if desired. The display 184 comprises any suitable technology for displaying information, including, but not limited to, a liquid crystal display (LCD), organic light emitting diode (OLED), plasma, or a cathode ray tube (CRT). In this example, the display 184 is an electronic display capable of graphically displaying one or more user interfaces under the control of the controller 138. Those skilled in the art may realize other techniques to implement the display 184 on the trolley 120.

The controller 138 includes at least one processor 186 and a computer-readable storage device or media 188. The processor 186 may be any custom-made or commercially available processor, a central processing unit (CPU), a graphics processing unit (GPU), an application specific integrated circuit (ASIC) (e.g., a custom ASIC implementing a neural network), a field programmable gate array (FPGA), an auxiliary processor among several processors associated with the controller 138, a semiconductor-based microprocessor (in the form of a microchip or chip set), any combination thereof, or generally any device for executing instructions. The computer readable storage device or media 188 may include volatile and nonvolatile storage in read-only memory (ROM), random-access memory (RAM), and keep-alive memory (KAM), for example. KAM is a persistent or non-volatile memory that may be used to store various operating variables while the processor 186 is powered down. The computer-readable storage device or media 188 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 138 in controlling the mobile sanitization system 100. In various embodiments, controller 138 is configured to implement instructions of sanitization control system 300 as discussed in detail below.

In various embodiments, the instructions, when executed by the processor 186, receive and process input data received from the human-machine interface 136 to disinfect and sanitize the surfaces associated with the mobile platform 102 as the mobile sanitization system 100 travels along the aisle 106. The instructions determine whether it is selected to use at least one of the light sources 190, the nozzles (the trolley nozzles 176 and the arm nozzles 192) and the spray wand 178 to disinfect and sanitize the surfaces associated with the mobile platform 102 and controls the mobile sanitization system 100 to travel along the aisle 106 based on the selection.

In one example, the trolley 120 includes the arm drive system 140. The arm drive system 140 may comprise any suitable electro-mechanical system configured to move the extendable arms 122a, 122b from a first position, in which the arms 122a, 122b are in a collapsed state within the trolley 120 so as to be contained within a footprint defined by the housing 124 of the trolley 120, to a second position, in which the arms 122a, 122b are extended outwardly away from the trolley 120 and suspended above the surfaces of the passenger seats 104 and below the surfaces of the stowage compartments 108. In one example, the arm drive system 140 includes two linear actuators 140a, 140b that are responsive to control signals from the controller 138 to move the arms 122a, 122b relative to the trolley 120. The linear actuators 140a, 140b are each in communication with the controller 138 over a suitable communication architecture that supports the transfer of data and power, including, but not limited to a bus. As will be discussed, the linear actuators 140a, 140b are responsive to control signals from the controller 138 to move the arms 122a, 122b from the first position in the collapsed state to the second position in the extended state and vice versa. It should be noted that while the linear actuators 140a, 140b are described herein as moving the extendable arms 122a, 122b between the first position and the second position, the linear actuators 140a, 140b may also be used to move the extendable arms 122a, 122b into positions between the first position and the second position, depending upon the desired extension of the extendable arms 122a, 122b.

The extendable arms 122a, 122b are movably coupled to the trolley 120. In one example, each of the extendable arms 122a, 122b include the light sources 190, the arm nozzles 192 and one or more arm proximity sensors 195. The light sources 190, the arm nozzles 192 and the arm proximity sensors 195 are supported on a respective arm support structure 194. In one example, each of the arm support structures 194 comprise a horizontal scissors mechanism, which is coupled to a respective one of the linear actuators 140a, 140b and to the housing 124. An extension of the respective linear actuator 140a, 140b moves or drives the horizontal scissors mechanism outward from the first position to the second position. In one example, the light sources 190 comprise one to about fourteen Ultraviolet C (UVC) light sources, which when illuminated, disinfect air and the surfaces of the mobile platform 102 that are within a beam path of the light emitted by the light sources 190. Thus, the light sources 190 generally sanitize surfaces within a line of sight of the respective light source 190, while the trolley nozzles 176, the arm nozzles 192 and the spray wand 178 sanitize and disinfect surfaces that are not within a line of sight to ensure that all of the surfaces of the cabin 103 are disinfected. Each of the light sources 190 are in communication with the controller 138 over a suitable communication architecture that supports the transfer of data and power, including, but not limited to a bus. The light output by each of the light sources 190 is adjustable based on the control signals received from the controller 138. For example, the voltage into a respective light source 190 may determine a corresponding illumination of the particular light source 190. As will be discussed, the light sources 190 are responsive to control signals from the controller 138 to illuminate. The light sources 190 are generally coupled to the arm support structure 194 via one or more mechanical fasteners, such as bolts, screws, etc.

The arm nozzles 192 are also coupled to the arm support structure 194 of each of the arms 122a, 122b via one or more mechanical fasteners, for example. In one example, the arm nozzles 192 are coupled to the arm support structure 194 to extend along a perimeter of the arm support structure 194. By coupling the arm nozzles 192 along the perimeter of the arm support structure 194, the arm nozzles 192 may spray the liquid disinfectant along a sidewall of the cabin 103, along the passenger seats 104 and the stowage compartments 108. In one example, each of the arm nozzles 192 includes, but is not limited to, a spray nozzle, misting nozzle, fogging nozzle, electrostatic nozzle, or high-volume nozzle, either with a full cone or hollow cone pattern. Each of the arm nozzles 192 is fluidly coupled to the valve 174 via a respective hose, fluid coupling, etc. It should be noted that a manifold may be coupled between the valve 174 and the arm nozzles 192 to assist in directing the liquid disinfectant from the valve 174 to each of the arm nozzles 192. In one example, each of the arm support structures 194 may include one to about four arm nozzles 192 coupled to the respective arm support structure 194 about the perimeter of the arm support structure 194. Generally, the spray of each of the arm nozzles 192 may be about 3 feet to about 5 feet. It should be noted, that if desired, one or more of the arm nozzles 192 may be coupled to the arm support structure 194 at other locations along the arms 122a, 122b. For example, arm nozzles 192 may be coupled in between the light sources 190 in a center of the arm support structure 194 to face upward toward the stowage compartments 108 to assist in cleaning the stowage compartments 108 and surfaces above the passenger seats 104, such as passenger control panels. The arm nozzles 192 may also be coupled in between the light sources 190 in a center of the arm support structure 194 to face downward toward the passenger seats 104 to assist in cleaning in between the passenger seats 104 and surfaces of the cabin 103 below the passenger seats 104. Other sources on the arms may be pointed upward to assist in cleaning the passenger service unit and other over-head high-touch surfaces, such as one or more of the arm nozzles 192 and/or one or more of the light sources 190. The arm nozzles 192 may have a varying flow due to a speed of the pump 172 or nozzle opening of the respective arm nozzles 192.

Each of the arms 122a, 122b includes the arm proximity sensors 195. In one example, each of the arms 122a, 122b includes one or more of the arm proximity sensors 195 at an end surface of the arm 122a, 122b; at a top surface of the arm 122a, 122b; and at a bottom surface of the arm 122a, 122b. It should be noted that in other examples, each of the arms 122a, 122b may include a single one of the arm proximity sensors 195, if desired. The arm proximity sensors 195 may comprise an infrared sensor, however, other distancing sensors may be employed, including, but not limited to, lidar, radar, etc. Generally, each of the arm proximity sensors 195 observe a distance between the respective surface of the arm 122a, 122b and a surface within the mobile platform 102, such as surfaces of the passenger seat 104 (seatback, seating surface, seat arm), the stowage compartments 108, etc. and generate sensor signals based on the observations. Each of the arm proximity sensors 195 are in communication with the controller 138 over a suitable communication architecture that supports the transfer of data and power, including, but not limited to a bus. As will be discussed, the position of the surface of the arm 122a, 122b relative to the surface within the mobile platform 102 may be used by the controller 138 to adjust an illumination output by the light sources 190.

Figure 2:
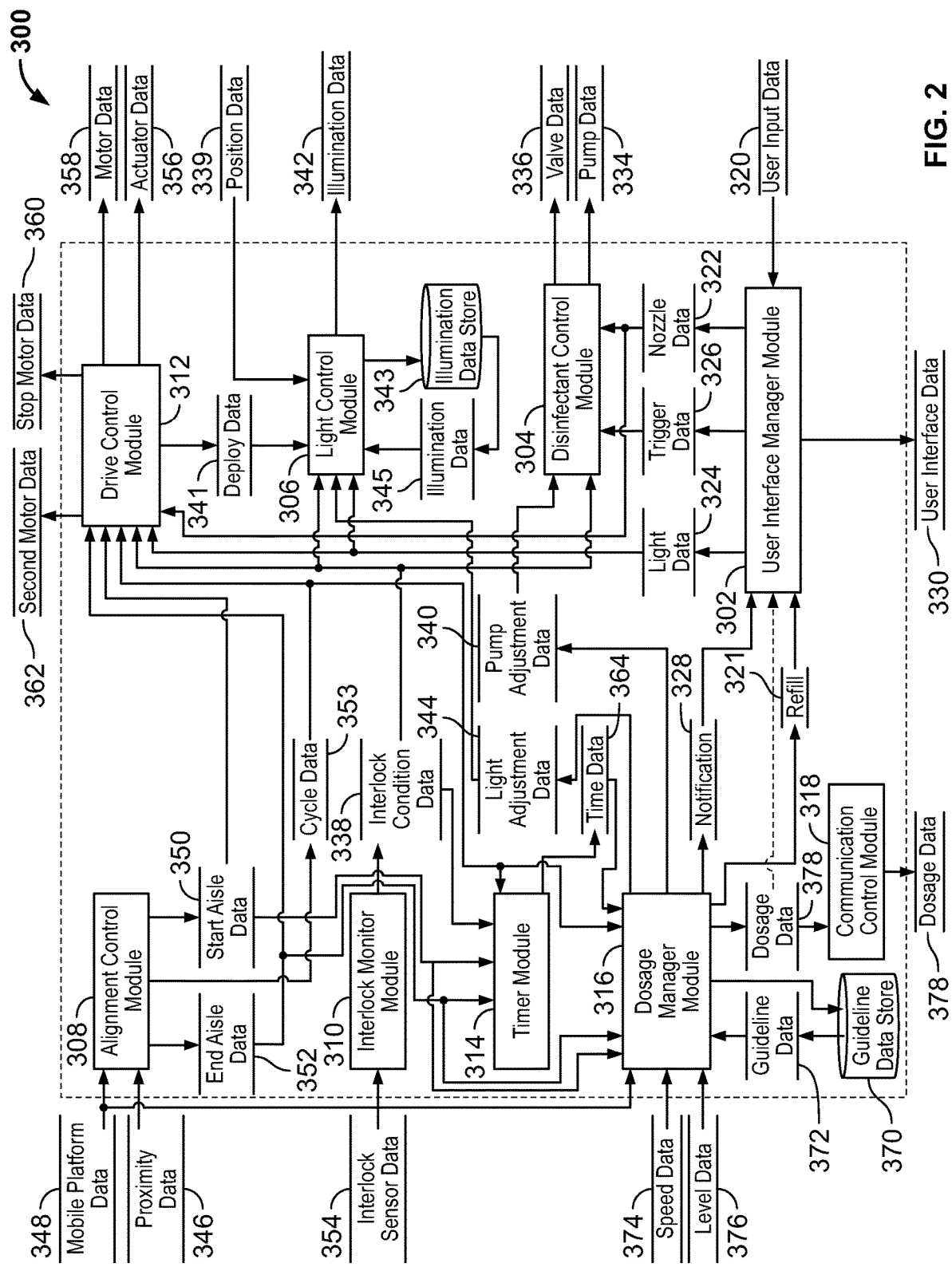
FIG. 2 is a dataflow diagram illustrating a sanitization control system for the mobile sanitization system in accordance with various embodiments.

With reference now to FIG. 2 and with continued reference to FIG. 1, FIG. 2 is a dataflow diagram illustrating aspects of the sanitization control system 300 for the mobile sanitization system 100, which is embedded within the controller 138. As can be appreciated, the modules and sub-modules shown in FIG. 2 can be combined and/or further partitioned to similarly perform the functions described herein. Inputs to modules and sub-modules may be received from the sensors 128, received from other control modules (not shown) associated with the mobile sanitization system 100, received from the human-machine interface 136, received from the communication system 134, received from the trigger 178a and/or determined/modeled by other sub-modules (not shown) within the controller 138 of FIG. 1. The modules and sub-modules shown generally perform the functions of controlling the mobile sanitization system 100 to disinfect or sanitize the mobile platform 102. As shown in FIG. 2, the sanitization control system 300 includes a user interface (UI) manager module 302, a disinfectant control module 304, a light control module 306, an alignment control module 308, an interlock monitor module 310, a drive control module 312, a timer module 314, a dosage manager module 316 and a communication control module 318.

The UI manager module 302 receives as input user input data 320 from the human-machine interface 136. The UI manager module 302 processes the user input data 320 and determines whether input has been received to activate the trolley nozzles 176 and the arm nozzles 192. If true, the UI manager module 302 sets nozzle data 322 for the disinfectant control module 304 and the drive control module 312. The nozzle data 322 indicates that a request to activate the trolley nozzles 176 and the arm nozzles 192 has been received. The UI manager module 302 also processes the user input data 320 to determine whether input has been received to activate the light sources 190. If true, the UI manager module 302 sets light data 324 for the light control module 306 and the drive control module 312. The light data 324 indicates that a request to activate the light sources 190 has been received. The UI manager module 302 also processes the user input data 320 to determine whether input has been received to the trigger 178a to activate the spray wand 178. If true, the UI manager module 302 sets trigger data 326 for the disinfectant control module 304. The trigger data 326 indicates that a request to activate the spray wand 178 has been received via a user's input to the trigger 178a of the spray wand 178.

The UI manager module 302 also receives as input notification 328. The notification 328 indicates that a function of the mobile sanitization system 100 has been changed to meet dosage guidelines. For example, the notification 328 may comprise data that indicates an output of the light sources 190 has been reduced or increased to meet dosage guidelines. The notification 328 may also include data that indicates that an output of the trolley nozzles 176 and the arm nozzles 192 has been reduced or increased to meet dosage guidelines. Upon receipt of the notification 328, the UI manager module 302 generates and outputs user interface data 330 for rendering a user interface on the display 184 associated with the human-machine interface 136. The user interface data 330 may comprise a user interface containing text and/or graphics that indicate the change in the light output and/or nozzle output due to the dosage guidelines. The UI manager module 302 may optionally receive as input dosage data 332 from the dosage manager module 316. The dosage data 332 indicates an amount of liquid disinfectant output during the operation of the mobile sanitization system 100 and a percent reduction in microbial amount based on the light output by the light sources 190. The UI manager module 302 may also generate and output the user interface data 330 for rendering the user interface on the display 184, which includes the dosage data 332.

The UI manager module 302 also receives as input refill 321. The refill 321 indicates that additional liquid disinfectant is needed in the reservoir 170 prior to the beginning of a cleaning cycle. Upon receipt of the refill 321, the UI manager module 302 generates and outputs the user interface data 330 for rendering the user interface on the display 184 associated with the human-machine interface 136. The user interface data 330 may comprise the user interface with text and/or graphics that indicate that additional liquid disinfectant is needed in the reservoir 170.

The disinfectant control module 304 receives as input interlock condition data 338 from the interlock monitor module 310 and the nozzle data 322. The interlock condition data 338 indicates whether an interlock condition is satisfied. If the interlock condition data 338 indicates true or that the interlock condition is satisfied, based on the nozzle data 322, the disinfectant control module 304 outputs pump data 334 and valve data 336. The pump data 334 is one or more control signals for the pump 172 to activate the pump 172 at a predefined flow rate to draw the liquid disinfectant from the reservoir 170. The valve data 336 is one or more control signals to the valve 174 to move the valve 174 from the current position of the valve 174 to the opposite position of the valve 174 (from the second, closed position to the first, opened position and vice versa). Generally, the valve 174 is in the second, closed position at a start-up of the mobile sanitization system 100 such that the valve data 336 moves the valve 174 from the second, closed position to the first, opened position. If the interlock condition data 338 indicates false or that the interlock condition is unsatisfied, the disinfectant control module 304 outputs the valve data 336 if the valve 174 is not in the second, closed position, based on sensor signals received from the position sensor associated with the valve 174, for example.

The disinfectant control module 304 also receives as input trigger data 326. Based on the trigger data 326, the disinfectant control module 304 sets the pump data 334 for the pump 172. The disinfectant control module 304 receives as input pump adjustment data 340 from the dosage manager module 316. The pump adjustment data 340 indicates an adjusted flow rate for the pump 172 to adjust the output of the trolley nozzles 176 and the arm nozzles 192. Based on the receipt of the pump adjustment data 340, the disinfectant control module 304 outputs the pump data 334 to the pump 172 for the pump 172 to operate at the adjusted flow rate. For example, the pump 172 has a first predefined flow rate or initial predetermined flow rate for a standard speed of the mobile sanitization system 100 along the aisle 106, and the pump adjustment data 340 may comprise a reduced flow rate to compensate for a reduced speed of the trolley 120 along the aisle 106. Conversely, the pump adjustment data 340 may comprise an increased flow rate to compensate for an increased speed of the trolley 120 along the aisle 106 to ensure the surfaces are disinfected.

The light control module 306 receives as input the interlock condition data 338 from the interlock monitor module 310, the light data 324 and position data 339. The light control module 306 also receives as input deploy data 341 from the drive control module 312. The deploy data 341 indicates whether the arms 122a, 122b have been deployed. The position data 339 comprises the sensor signals from the arm proximity sensors 195. The light control module 306 processes the position data 339 and determines the distance between the respective surface of the respective arm 122a, 122b and the surface within the mobile platform 102. If the interlock condition data 338 indicates true or that the interlock condition is satisfied and the arms have been deployed based on the deploy data 341, based on the receipt of the light data 324 and the determined position of the respective surfaces of the respective arms 122a, 122b, the light control module 306 queries an illumination datastore 343 and retrieves illumination output data 345.

Generally, the illumination datastore 343 stores one or more look-up tables that provide, for a particular observed distance between the respective surface of the respective arm 122a, 122b and the respective surface within the mobile platform 102, the amount of illumination for the light sources 190 to ensure sanitization without over exposure of the surface within the mobile platform 102. Thus, the one or more look-up tables store illumination output data 345 indicating an amount of illumination for the light sources 190 based on the position data 339. The illumination output data 345 are predefined or factory-set values, which are pre-populated. It should be noted that in the example where a single arm proximity sensor 195 is employed with each of the arms 122a, 122b, the illumination datastore 343 may store data that provides, for a particular observed distance between the respective arm 122a, 122b and the surface within the mobile platform 102, the amount of illumination for the light sources 190 associated with the respective arm 122a, 122b to ensure sanitization without over exposure of the surface within the mobile platform 102.

Based on the retrieved illumination output data 345, the light control module 306 outputs illumination data 342. The illumination data 342 is one or more control signals for the light sources 190 to activate the light sources 190 to illuminate at the output retrieved from the illumination datastore 343. If the interlock condition data 338 indicates false or that the interlock condition is unsatisfied, the light control module 306 waits for the interlock condition data 338 to be true before outputting the illumination data 342 or ceases outputting the illumination data 342.

The light control module 306 also receives as input light adjustment data 344 from the dosage manager module 316. The light adjustment data 344 indicates an adjusted amount of illumination for the light sources 190 to adjust the illumination output by the light sources 190. Based on the receipt of the light adjustment data 344, the light control module 306 outputs the illumination data 342 to the light sources 190 to operate at the adjusted amount of illumination. For example, if the light sources 190 have a first predefined amount of illumination for a standard speed of the mobile sanitization system 100 along the aisle 106, the light adjustment data 344 may comprise a reduced amount of illumination or percent reduction of the illumination output to compensate for a reduced speed of the trolley 120 along the aisle 106, which may protect the surfaces in the cabin 103 from overexposure. Conversely, the light adjustment data 344 may comprise an increased amount of illumination or percent increase of the illumination output to compensate for an increased speed of the trolley 120 along the aisle 106 to ensure the surfaces are disinfected and sanitized. Thus, the dosage, or the product of the exposure time to illumination, is kept constant.

The alignment control module 308 receives as input proximity data 346. The proximity data 346 comprises the sensor signals from the proximity sensors 160. The alignment control module 308 also receives as input mobile platform data 348. The mobile platform data 348 is data regarding the mobile platform 102, which may be received from other modules associated with the controller 138, may be pre-defined and stored in the media 188, or may be received from the communication control module 318. The mobile platform data 348 generally includes a width of the aisle 106 or a distance between the passenger seats 104 that line the aisle 106. The mobile platform data 348 may also include a length of the aisle 106 from a start of the aisle 106 to an end of the aisle 106. The mobile platform data 348 also includes an identifier of the type of mobile platform 102, such as the make and/or model. The mobile platform data 348 also includes an amount of liquid disinfectant needed to disinfect the surfaces of the mobile platform 102. For example, if one gallon of liquid disinfectant is needed to disinfect about 150 square feet to about 1000 square feet, for the mobile platform 102 that comprises a single aisle aircraft, the amount of liquid disinfectant is about 5 gallons to about 10 gallons based on an interior or cabin surface area of about 2550 square feet to about 5000 square feet. As a further example, if one gallon of liquid disinfectant is needed to disinfect about 150 square feet to about 1000 square feet, for the mobile platform 102 that comprises a double aisle aircraft, the amount of liquid disinfectant is about 8 gallons to about 16 gallons based on an interior or cabin surface area of about 4150 square feet to about 8000 square feet.

Based on the mobile platform data 348 and the proximity data 346, the alignment control module 308 determines whether the trolley 120 is aligned with a start of the aisle 106 and if the trolley 120 is centered within in the aisle 106. For example, the method determines whether the proximity data 346 indicates that the passenger seats 104 are equally positioned on opposed sides of the trolley 120 and that no passenger seats 104 are in proximity to a rear of the trolley 120 in a direction of travel of the trolley 120. If true, the alignment control module 308 sets start aisle data 350 for the drive control module 312 and the timer module 314. The start aisle data 350 indicates the trolley 120 is positioned at the start of the aisle 106 of the mobile platform 102. If false, in certain embodiments, a notification may be output to the display 184 to instruct the operator to reposition the trolley 120. Alternatively, one or more control signals may be output to the wheel drive system 152a, 152b to drive the pairs of wheels 150a, 150b as needed to position the trolley 120 within the center of the aisle 106 at the start of the aisle 106.

Based on the mobile platform data 348 and the proximity data 346, the alignment control module 308 determines whether the trolley 120 is aligned and centered with an end of the aisle 106. For example, the method determines whether the proximity data 346 indicates that the passenger seats 104 are equally positioned on opposed sides of the trolley 120 and that no passenger seats 104 are in proximity to a front of the trolley 120 in the direction of travel of the trolley 120. If true, the alignment control module 308 sets end aisle data 352 for the drive control module 312, the timer module 314 and the dosage manager module 416. The end aisle data 352 indicates the trolley 120 is positioned at the end of the aisle 106 of the mobile platform 102. The alignment control module 308 also sets cycle data 353 for the drive control module 312 and the timer module 314. The cycle data 353 indicates that a cleaning cycle is complete. Generally, the alignment control module 308 sets the cycle data 353 once the alignment control module 308 has determined that the trolley is aligned with the start of the aisle 106 after being aligned with the end of the aisle 106. Stated another way, the alignment control module 308 sets the cycle data 353 at the next determination of an alignment of the start of the aisle 106 after a determination of an alignment with the end of the aisle 106. Thus, generally, a cleaning cycle is a pass of the trolley up and down (or forward and back) along a respective aisle 106. It should be noted, however, that due to the spray wand 178, the trolley 120 may complete a cleaning cycle in a single pass or movement down the aisle 106 such that a return pass is not necessary. Thus, although the cleaning cycle is described herein as a movement of the trolley up and down the aisle 106, the cleaning cycle may be completed in a single trip down the aisle 106.

The interlock monitor module 310 receives as input interlock sensor data 354. The interlock sensor data 354 comprises the sensor signals from the interlock sensors 164. Based on the interlock sensor data 354, the interlock monitor module 310 determines whether the operator's hand is on the handle 142a, 142b and sets the interlock condition data 338 for the timer module 314, the drive control module 312, the light control module 306 and the disinfectant control module 304 based on this determination. As discussed, in one example, the interlock condition data 338 is true if the interlock monitor module 310 determines based on the interlock sensor data 354 that the operator's hand is on one of the handles 142a, 142b; and the interlock condition data 338 is false if the interlock monitor module 310 determines based on the interlock sensor data 354 that the operator's hand is not on the handles 142a, 142b.

The drive control module 312 receives as input the start aisle data 350, the interlock condition data 338, the light data 324 and/or the nozzle data 322. Based on the interlock condition data 338 as true, the start aisle data 350, the light data 324 and/or the nozzle data 322, the drive control module 312 outputs actuator data 356 and first motor data 358. The actuator data 356 is one or more control signals to the linear actuators 140a, 140b of the arms 122a, 122b to activate the linear actuators 140a, 140b to move the arms 122a, 122b relative to the trolley 120 from the first position to the second position. The first motor data 358 is one or more control signals to the first wheel drive system 152a to rotate to the wheel 150 of the first pair of wheels 150a to move the trolley 120 along the aisle 106 in a first direction. Based on the output of the actuator data 356, the drive control module 312 also sets the deploy data 341 for the light control module 306.

The drive control module 312 receives as input the start aisle data 350 and the interlock condition data 338. Based on the interlock condition data 338 as true and the start aisle data 350, the drive control module 312 outputs the first motor data 358. The first motor data 358 is one or more control signals to the first wheel drive system 152a to rotate to the wheel 150 of the first pair of wheels 150a to move the trolley 120 along the aisle 106 in a first direction.

The drive control module 312 receives as input the end aisle data 352 and the interlock condition data 338. Based on the receipt of the end aisle data 352 and the interlock condition data 338 as false, the drive control module 312 outputs stop motor data 360. The stop motor data 360 is one or more control signals to the first wheel drive system 152a to stop a rotation of the first pair of wheels 150a such that a motion of the trolley 120 along the aisle 106 in a first direction is halted. Based on the receipt of the end aisle data 352 and the interlock condition data 338 as true, the drive control module 312 outputs second motor data 362. The second motor data 362 is one or more control signals to the second wheel drive system 152b to rotate to the wheel 150 of the second pair of wheels 150b to move the trolley 120 along the aisle 106 in a second direction, which is opposite the first direction.

The drive control module 312 receives as input the cycle data 353 and the light data 324 and/or the nozzle data 322. Based on the receipt of the cycle data 353 and the light data 324 and/or the nozzle data 322, the drive control module 312 outputs the stop motor data 360 and the actuator data 356 to move the arms 122a, 122b relative to the trolley 120 from the second position to the first position. The drive control module 312 also receives as input the cycle data 353. Based on the receipt of the cycle data 353, the drive control module 312 outputs the stop motor data 360. Thus, the drive control module 312 controls the pair of wheels 150a, 150b to move the trolley 120 independently of the activation of the light sources 190, the trolley nozzles 176 and the arm nozzles 192.

The timer module 314 receives as input start aisle data 350 and interlock condition data 338. Based on the start aisle data 350 and interlock condition data 338 as true, the timer module 314 starts a timer. Based on a change in the interlock condition data 338 from true to false received during the running of the timer, the timer module 314 pauses the timer. The timer module 314 outputs time data 364 as the timer runs to the dosage manager module 316. The time data 364 is the time of operation of the mobile sanitization system 100 within the cabin 103 along the aisle 106 in one direction. The timer module 314 also receives as input end aisle data 352. Based on the receipt of the end aisle data 352, the timer module 314 resets the timer. The timer module 314 also receives as input cycle data 353. Based on the receipt of the cycle data 353, the timer module 314 also resets the timer.

A guidelines datastore 370 stores one or more look-up tables that provide, for a particular mobile platform 102, the amount of illumination for the light sources 190 and the flow rate for the pump 172 based on a particular rate of travel of the trolley 120 along the length of the aisle 106. Thus, the one or more look-up tables store guideline data 372 indicating an amount of illumination for the light sources 190 and the flow rate for the pump 172 based on a rate of travel the trolley 120 to sanitize the surfaces along a particular aisle 106 of the particular mobile platform 102. The guideline data 372 are predefined or factory-set values, which are pre-populated. Alternatively, the guideline data 372 may be predefined by a user at the other entities 180 and communicated to the mobile sanitization system 100 via the communication system 134 and populated within the guidelines datastore 370, for example. In one example, the guidelines datastore 370 stores the amount of illumination for the light sources 190 and the flow rate for the pump 172 based on a rate of travel of the trolley 120 from 10 rows per minute to 30 rows per minute. For example, for both a single aisle and twin aisle aircraft, the flow rate of disinfectant is about 1 gallon per minute to about 3 gallons per minute at a rate of travel of the trolley 120 of 10 rows per minute. The illumination of the light sources 190 is about 2.5 milliwatts (mW) to about 6 milliwatts (mW) at a rate of travel of the trolley 120 of 10 rows per minute, as measured at the exposed target.

The dosage manager module 316 receives as input the mobile platform data 348, speed data 374, the time data 364, level data 376 and the start aisle data 350. The speed data 374 is the sensor signals from the wheel speed sensor 162. The level data 376 is the sensor signals from the level sensor 170a of the reservoir 170. Based on the start aisle data 350 and the level data 276, the dosage manager module 316 determines the amount of fluid remaining in the reservoir 170. The dosage manager module 316 determines, based on the mobile platform data 348, whether the amount of fluid remaining in the reservoir 170 is sufficient to complete a cleaning cycle. Stated another way, the dosage manager module 316 compares the amount of fluid in the reservoir 170 from the level sensor 170a to an amount of fluid required to clean the mobile platform 100 from the mobile platform data 348. If the amount of fluid in the reservoir 170 is less than the amount of fluid needed to clean the mobile platform 100, the dosage manager module 316 sets refill 321 for the UI manager module 302. The refill 321 is a notification for display on the display 184 to inform the user to refill the reservoir 170 prior to starting the cleaning cycle.

Based on the start aisle data 350, the dosage manager module 316 determines a rate of travel of the trolley 120 down the aisle 106. The rate of travel is determined based on dividing the speed data 374 by the time data 364. Based on the mobile platform data 348 and the rate of travel, the dosage manager module 316 queries the guideline datastore 370 and retrieves guideline data 372 associated with the mobile platform 102. The dosage manager module 316 determines, based on the guideline data 372 and the rate of travel of the trolley 120, the amount of illumination for the light sources 190 and the flow rate for the pump 172. If the amount of illumination retrieved for the light sources 190 is different than a current amount of illumination for the light sources 190 (which is a stored in a memory associated with the dosage manager module 316), the dosage manager module 316 sets the light adjustment data 344 for the light control module 306 based on the difference between the current amount of illumination and the retrieved amount of illumination. If the flow rate retrieved for the pump 172 is different than a current flow rate for the pump 172 (which is stored in a memory associated with the dosage manager module 316), the dosage manager module 316 sets the pump adjustment data 340 for the disinfectant control module 304 based on the difference between the current flow rate and the retrieved flow rate. During a start-up of the trolley 120, the initial flow rate of the pump 172 is predefined or factory set, at about 1 gallon per minute to about 3 gallons per minute; and the illumination output by the light sources 190 is about 2.5 milliwatts (mW) to about 6 milliwatts (mW). The dosage manager module 316 sets the notification 328 for the UI manager module 302. Based on the start aisle data 350, the dosage manager module 316 sets the level data 376 as an initial fluid level for the reservoir 170.

The dosage manager module 316 receives as input the end aisle data 352. Based on the end aisle data 352, the dosage manager module 316 awaits for receipt of time data 364 greater than zero, which indicates the trolley 120 has begun moving back up the aisle 106. Based on receipt of the time data 364 greater than zero, the dosage manager module 316 determines the rate of travel of the trolley 120 down the aisle 106 based on the time data 364 and the speed data 374. The dosage manager module 316 determines based on the guideline data 372 and the rate of travel of the trolley 120, the amount of illumination for the light sources 190 and the flow rate for the pump 172. If the amount of illumination retrieved for the light sources 190 is different than the current amount of illumination for the light sources 190, the dosage manager module 316 sets the light adjustment data 344 for the light control module 306. If the flow rate retrieved for the pump 172 is different than current flow rate for the pump 172, the dosage manager module 316 sets the pump adjustment data 340 for the disinfectant control module 304. The dosage manager module 316 sets the notification 328 for the UI manager module 302.

The dosage manager module 316 also receives as input the cycle data 353. Based on the cycle data 353, the dosage manager module 316 receives as input level data 376. The dosage manager module 316 determines a change in the fluid level of the reservoir 170 by subtracting the initial fluid level from the fluid level at the end of the cleaning cycle. The dosage manager module 316 sets the difference between the initial fluid level and the fluid level at the end of the cleaning cycle as dosage data 378 for the communication control module 318 as the liquid disinfectant dosage. In certain instances, the dosage manager module 316 may query a datastore and retrieve a percent disinfection based on the volume of liquid disinfectant dispensed and the given surface area of the mobile platform 102 from the mobile platform data 348 (e.g. a percent disinfection for the mobile platform 102 based on gallons per square feet dispensed). The dosage manager module 316 also determines a light dosage and includes the determined light dosage as dosage data 378. The light dosage is determined based on pre-set factory values that provide a percent reduction in a microbial amount (e.g. bacteria colonies) as a function of time for a given illumination output (light energy). Based on the time data 364 and the cycle data 353, the dosage manager module 316 determines a time of the illumination of the light sources 190 during the cleaning cycle. Given the time of illumination of the light sources 190 and the illumination output by the light sources 190, the dosage manager module 316 determines the light dosage as the percent reduction in a microbial amount based on the pre-set factory values. For example, the dosage manager module 316 may query a datastore that stores a look-up table, which provides the light dosage or percent reduction in a microbial amount for a particular time of illumination and a particular illumination output by the light sources 190. Thus, generally, the dosage data 378 includes at least one of the amount of liquid disinfectant dispensed by the trolley nozzles 176, the arm nozzles 192 and the spray wand 178, and the percent reduction in a microbial amount from the light output by the light sources 190 at the end of a cleaning of the aisle 106.

The communication control module 318 receives as input the dosage data 378. Based on the receipt of the dosage data 378, the communication control module 318 outputs the dosage data 378 for communication to the other entities 180 via the communication system 134. In certain examples, the communication control module 318 may also receive as input data from the other entities 180 such as one or more commands to control the mobile sanitization system 100. For example, the light data 324 and the nozzle data 322 may be received as input from the other entities 180 via the communication control module 318, which may set the light data 324 and the nozzle data 322 for the light control module 306 and the disinfectant control module 304, respectively.

With reference now to FIGS. 3-6, and continued reference to FIGS. 1 and 2, a flowchart illustrates a control method 400 that may be performed by the sanitization control system 300 in accordance with various embodiments. In various embodiments, the control method 400 is performed by the processor 186 of the controller 138. As can be appreciated in light of the disclosure, the order of operation within the method is not limited to the sequential execution as illustrated in FIGS. 3-6 but may be performed in one or more varying orders as applicable and in accordance with the present disclosure. In various embodiments, the control method 400 can be scheduled to run based on one or more predetermined events, such as based upon receipt of the user input data 320.

Figure 3:
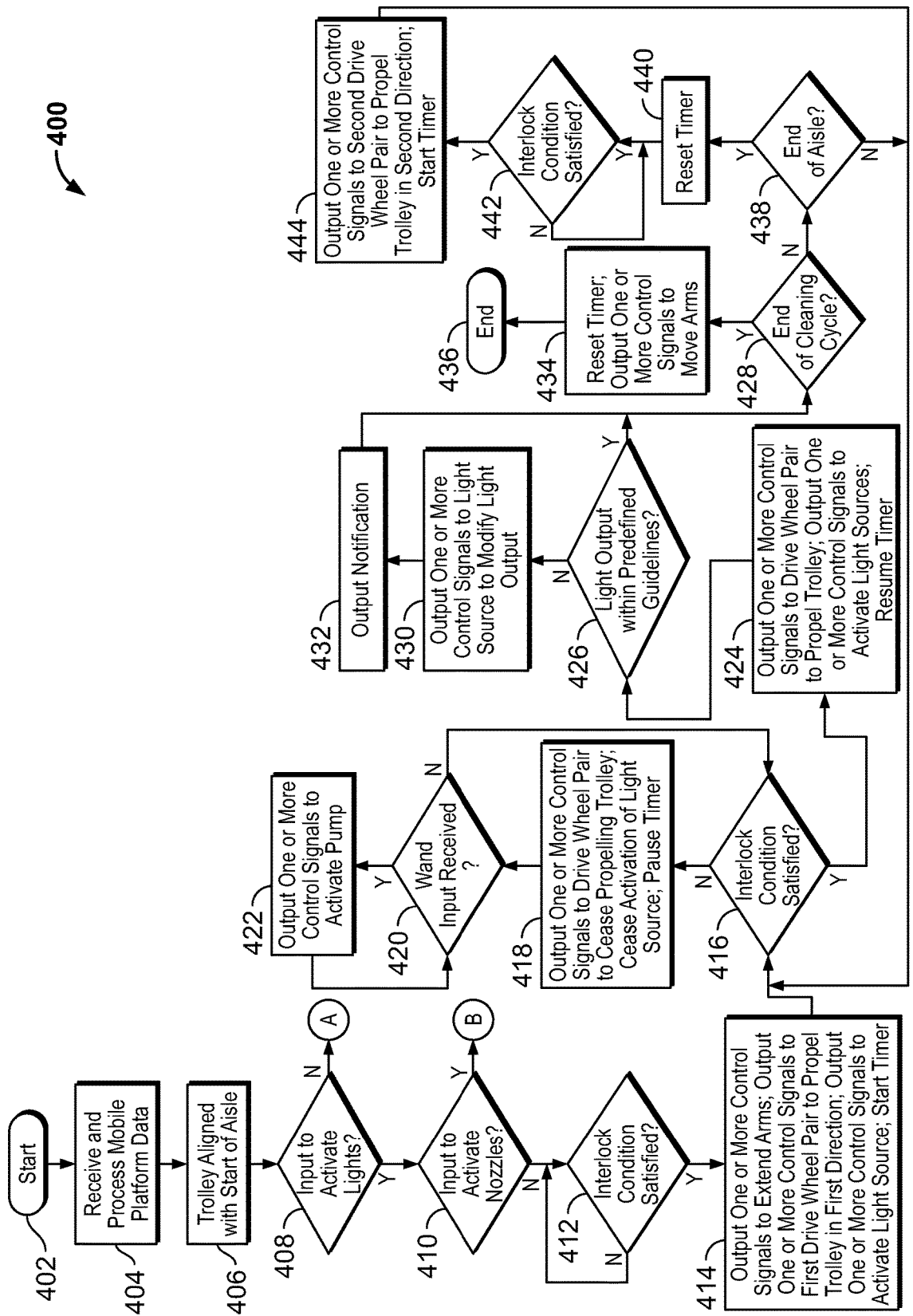
FIGS. 3-6 are flowcharts illustrating a control method that can be performed by the sanitization control system in accordance with various embodiments.

With reference to FIG. 3, the method begins at 402. At 404, the method receives and processes the mobile platform data 348. At 406, the trolley 120 is aligned and centered with the start of the aisle 106. As discussed, the location of the trolley 120 relative to the aisle 106 may be determined by the proximity sensors 160 and the mobile platform data 348. At 408, the method determines whether an input to activate the light sources 190 has been received to the human-machine interface 136. If false, the method proceeds to 410. Otherwise, the method proceeds to A on FIG. 4.

At 410, the method determines whether an input to activate the trolley nozzles 176 and the arm nozzles 192 has been received to the human-machine interface 136. If true, the method proceeds to B on FIG. 5. Otherwise, at 412, the method determines whether the interlock condition is satisfied or true based on the sensor signals from the interlock sensors 164. If false, the method loops. Otherwise, the method proceeds to 414.

At 414, the method outputs one or more control signals to the linear actuators 140a, 140b to move the arms 122a, 122b from the first position to the second position, and outputs one or more control signals to the first wheel drive system 152a to drive the wheel 150 of the first pair of wheels 150a to move the trolley 120 in the first direction. The method also receives the sensor signals from the arm proximity sensors 195 and determines the distance between the respective surface of the respective arm 122a, 122b and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method starts the timer.

At 416, the method determines whether the interlock condition is satisfied or true based on the sensor signals from the interlock sensors 164. If false or unsatisfied, the method proceeds to 418. Otherwise, the method proceeds to 420. At 418, the method outputs one or more control signals to stop the respective wheel drive system 152a, 152b to inhibit or halt the movement of the trolley 120. The method also ceases outputting the one or more control signals to the light sources 190 such that the light sources 190 are deactivated or are no longer illuminated. The method pauses the timer. At 420, the method determines whether input has been received to the trigger 178a of the spray wand 178 based on the signals from the trigger 178a. If true, the method proceeds to 422. Otherwise, the method loops to 416. At 422, the method outputs one or more control signals to the pump 172 to activate the pump 172 to dispense the liquid disinfectant through the spray wand 178.

At 416, if the interlock condition is satisfied or true, the method proceeds to 424. At 424, the method outputs the one or more control signals to the respective wheel drive system 152a, 152b to drive the one wheel 150 of the pair of wheels 150a, 150b to move the trolley 120 along the aisle 106. The method also receives the sensor signals from the arm proximity sensors 195 and determines the distance between the respective surface of the respective arm 122a, 122b and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method also resumes the timer. At 426, the method determines whether the amount of light output by the light sources 190 is within predefined guidelines based on the rate of travel of the trolley 120, the particular mobile platform 102 and the guideline data 372 retrieved from the guideline datastore 370. If true, the method proceeds to 428.

Otherwise, at 430, the method outputs one or more control signals to the light sources 190 at the modified amount of illumination of the light sources 190 from the light adjustment data 344. At 432, the method outputs the user interface data 330 to render the user interface including the notification on the display 184. For example, the user interface including the notification may textually or graphically indicate that the amount of illumination of the light sources 190 has been modified to account for the rate of travel of the trolley 120.

At 428, the method determines whether it is the end of the cleaning cycle or determines the cycle data 353. If true, at 434, the method resets the timer to zero, determines the dosage data 378 for the light output by the light sources 190, outputs the dosage data 378 to the other entities 180 and/or the display 184, outputs one or more control signals to the linear actuators 140a, 140b to move the arms 122a, 122b from the second position to the first position, and ends at 436. Otherwise, if false, at 438, the method determines whether the trolley 120 has reached the end of the aisle 106. If false, the method loops to 416. Otherwise, at 440, the method resets the timer. At 442, the method determines whether the interlock condition is satisfied. If false, the method loops. If true, at 444, the method outputs the one or more control signals to the wheel drive system 152b to drive the one wheel 150 of the pair of wheels 150b to move the trolley 120 along the aisle 106 in the second direction. The method also starts the timer. The method loops to 416.

Figure 4:
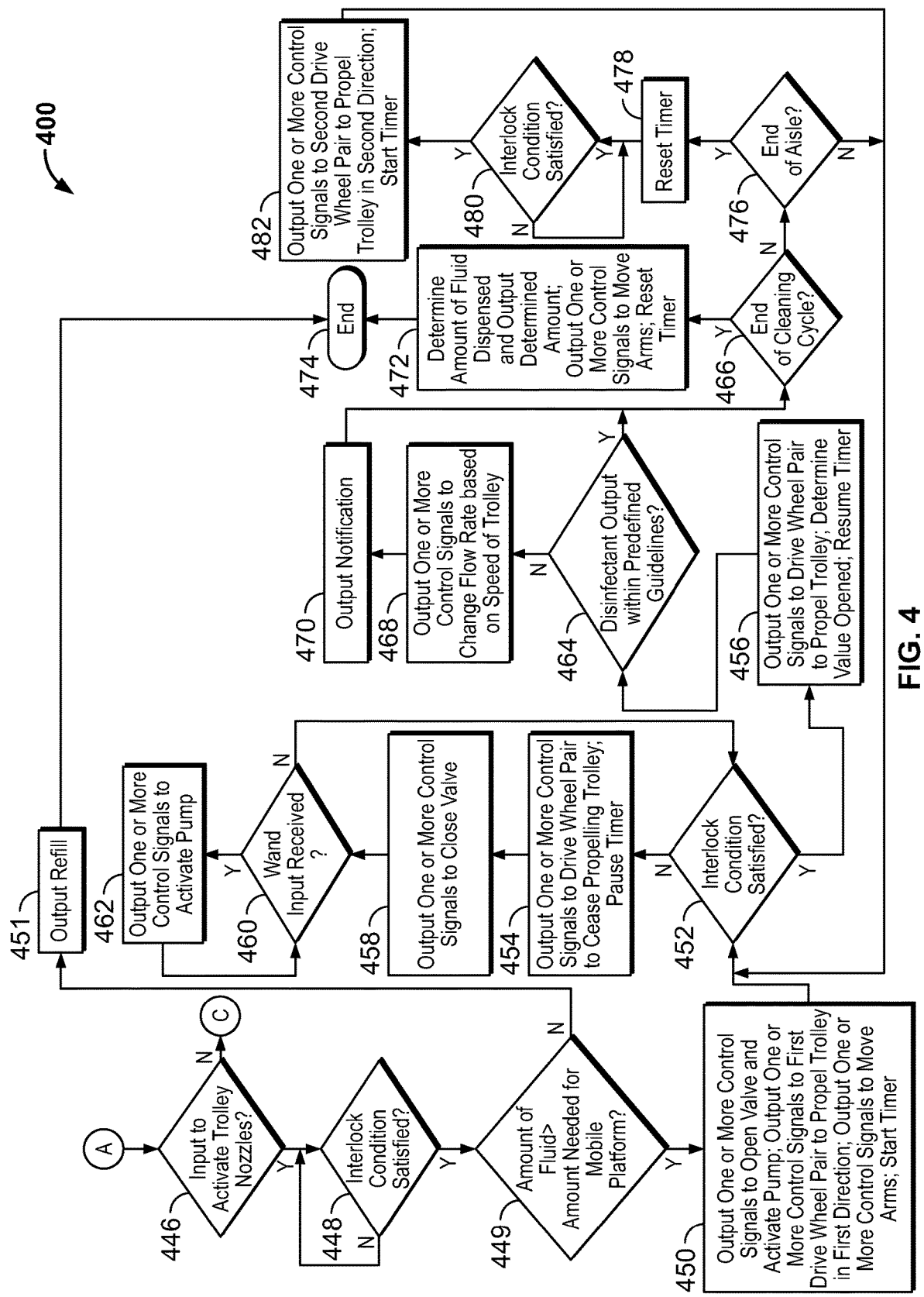

From A on FIG. 4, at 446, the method determines whether an input to activate the trolley nozzles 176 and the arm nozzles 192 has been received to the human-machine interface 136. If false, the method proceeds to C on FIG. 6. Otherwise, at 448, the method determines whether the interlock condition is satisfied or true based on the sensor signals from the interlock sensors 164. If false or unsatisfied, the method loops. Otherwise, the method proceeds to 449. At 449, the method determines the initial fluid level of the reservoir 170, and determines whether the initial fluid level is greater than the amount of fluid needed to complete a cleaning cycle or to disinfect the mobile platform based on the mobile platform data 348. If true, the method proceeds to 450. Otherwise, at 451, the method outputs the user interface data 330 that renders the user interface that indicates that a refill of the reservoir 170 is needed to complete the cleaning cycle. The method ends at 474.

At 450, the method outputs one or more control signals to the linear actuators 140a, 140b to move the arms 122a, 122b from the first position to the second position, outputs one or more control signals to open the valve 174, and outputs one or more control signals to activate the pump 172. The method also outputs the one or more control signals to the wheel drive system 152a to drive the one wheel 150 of the pair of wheels 150a to move the trolley 120 along the aisle 106 in the first direction. The method also starts the timer.

At 452, the method determines whether the interlock condition is satisfied or true based on the sensor signals from the interlock sensors 164. If false, the method proceeds to 454. Otherwise, the method proceeds to 456. At 454, the method outputs one or more control signals to stop the respective wheel drive system 152a, 152b to inhibit or halt the movement of the trolley 120. The method pauses the timer. At 458, the method outputs the one or more control signals to the valve 174 to move the valve 174 from the current position (first, opened position) to the opposite position (second, closed position). At 460, the method determines whether input has been received to the trigger 178a of the spray wand 178 based on the signals from the trigger 178a. If true, the method proceeds to 462. Otherwise, the method loops to 452. At 462, the method outputs one or more control signals to the pump 172 to activate the pump 172 to dispense the liquid disinfectant through the spray wand 178.

At 452, if the interlock condition is satisfied or true, the method proceeds to 456. At 456, the method outputs the one or more control signals to the respective wheel drive system 152a, 152b to drive the one wheel 150 of the pair of wheels 150a, 150b to move the trolley 120 along the aisle 106. The method determines whether the valve 174 is in the first, opened position, and if not, the method outputs the one or more control signals to the valve 174 to move the valve 174 to the first, opened position, based on the position of the valve 174 determined from the position sensor associated with the valve 174, for example. The method also resumes the timer. At 464, the method determines whether the amount of liquid disinfectant output by the pump 172 is within predefined guidelines based on the rate of travel of the trolley 120, the particular mobile platform 102 and the guideline data 372 retrieved from the guideline datastore 370. If true, the method proceeds to 466.

Otherwise, at 468, the method outputs one or more control signals to the pump 172 based on the modified flow rate of the pump 172 from the pump adjustment data 346. At 470, the method outputs the user interface data 330 to render the user interface including the notification on the display 184. For example, the user interface including the notification may textually or graphically indicate that the flow rate of the pump 172 has been modified to account for the rate of travel of the trolley 120.

At 472, the method determines whether it is the end of the cleaning cycle or determines the cycle data 353. If true, at 468, the method determines the amount of fluid dispensed by the trolley nozzles 176, the spray wand 178 and the arm nozzles 192 based on a difference between the initial fluid level value and the end fluid level value of the reservoir 170. The method determines the dosage data 378 for amount of liquid dispensed by the trolley nozzles 176, the spray wand 178 and the arm nozzles 192, and outputs the dosage data 378 to the other entities 180 and/or the display 184. The method resets the timer to zero, outputs one or more control signals to the linear actuators 140a, 140b to move the arms 122a, 122b from the second position to the first position, and ends at 474. Otherwise, if false, at 476, the method determines whether the trolley 120 has reached the end of the aisle 106. If false, the method loops to 452. Otherwise, at 478, the method resets the timer. At 480, the method determines whether the interlock condition is satisfied. If false, the method loops. If true, at 482, the method outputs the one or more control signals to the wheel drive system 152b to drive the one wheel 150 of the pair of wheels 150b to move the trolley 120 along the aisle 106 in the second direction. The method also starts the timer. The method loops to 452.

Figure 5:
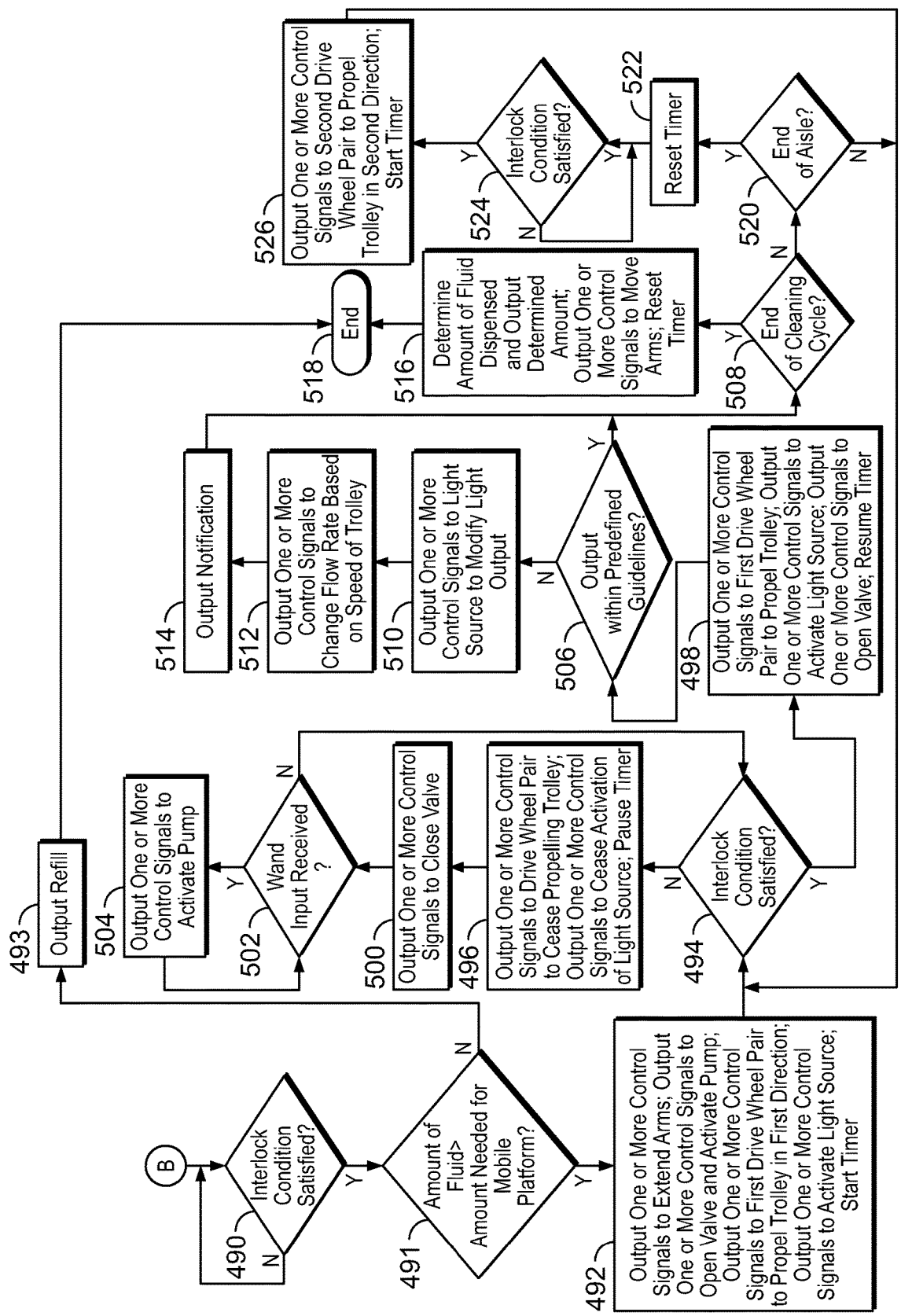

From B on FIG. 5, at 490, the method determines whether the interlock condition is satisfied or true based on the sensor signals from the interlock sensors 164. If false or unsatisfied, the method loops. Otherwise, the method proceeds to 491. At 491, the method determines the initial fluid level of the reservoir 170, and determines whether the initial fluid level is greater than the amount of fluid needed to complete a cleaning cycle or to disinfect the mobile platform based on the mobile platform data 348. If true, the method proceeds to 492. Otherwise, at 493, the method outputs the user interface data 330 that renders the user interface that indicates that a refill of the reservoir 170 is needed to complete the cleaning cycle. The method ends at 518.

At 492, the method outputs one or more control signals to the linear actuators 140*a*, 140*b* to move the arms 122*a*, 122*b* from the first position to the second position. The method also receives the sensor signals from the arm proximity sensors 195 and determines the distance between the respective surface of the respective arm 122*a*, 122*b* and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method also outputs one or more control signals to open the valve 174, and outputs one or more control signals to activate the pump 172. The method also outputs the one or more control signals to the wheel drive system 152*a* to drive the one wheel 150 of the pair of wheels 150*a* to move the trolley 120 along the aisle 106 in the first direction. The method also starts the timer.

At 494, the method determines whether the interlock condition is satisfied or true based on the sensor signals from the interlock sensors 164. If false, the method proceeds to 496. Otherwise, the method proceeds to 498. At 494, the method outputs one or more control signals to stop the respective wheel drive system 152*a*, 152*b* to inhibit or halt the movement of the trolley 120. The method also ceases outputting the one or more control signals to the light sources 190 such that the light sources 190 are deactivated or are no longer illuminated. The method pauses the timer. At 500, the method outputs the one or more control signals to the valve 174 to move the valve 174 from the current position (first, opened position) to the opposite position (second, closed position). At 502, the method determines whether input has been received to the trigger 178*a* of the spray wand 178 based on the signals from the trigger 178*a*. If true, the method proceeds to 504. Otherwise, the method loops to 494. At 504, the method outputs one or more control signals to the pump 172 to activate the pump 172 to dispense the liquid disinfectant through the spray wand 178.

At 498, if the interlock condition is satisfied or true, the method proceeds to 498. At 498, the method outputs the one or more control signals to the respective wheel drive system 152*a*, 152*b* to drive the one wheel 150 of the pair of wheels 150*a*, 150*b* to move the trolley 120 along the aisle 106. The method determines whether the valve 174 is in the first, opened position, and if not, the method outputs the one or more control signals to the valve 174 to move the valve 174 to the first, opened position. The method also receives the sensor signals from the arm proximity sensors 195 and determines the distance between the respective surface of the respective arm 122*a*, 122*b* and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method resumes the timer. At 506, the method determines whether the amount of light output by the light sources 190 and the amount of liquid disinfectant output by the pump 172 is within predefined guidelines based on the rate of travel of the trolley 120, the particular mobile platform 102 and the guideline data 372 retrieved from the guideline datastore 370. If true, the method proceeds to 508.

Otherwise, at 510, the method outputs one or more control signals to the light sources 190 at the modified amount of illumination of the light sources 190 from the light adjustment data 344. At 512, the method outputs one or more control signals to the pump 172 based on the modified flow rate of the pump 172 from the pump adjustment data 346. At 514, the method outputs the user interface data 330 to render the user interface including the notification on the display 184. For example, the user interface including the notification may textually or graphically indicate that the amount of illumination of the light sources 190 and the flow rate of the pump 172 has been modified to account for the rate of travel of the trolley 120.

At 508, the method determines whether it is the end of the cleaning cycle or determines the cycle data 353. If true, at 516, the method determines the amount of fluid dispensed by the trolley nozzles 176, the spray wand 178 and the arm nozzles 192 based on a difference between the initial fluid level value and the end fluid level value of the reservoir 170. The method determines the dosage data 378 for the light output by the light sources 190 and the amount of liquid dispensed by the trolley nozzles 176, the spray wand 178 and the arm nozzles 192, and outputs the dosage data 378 to the other entities 180 and/or the display 184. The method resets the timer to zero, outputs one or more control signals to the linear actuators 140*a*, 140*b* to move the arms 122*a*, 122*b* from the second position to the first position, and ends at 518. Otherwise, if false, at 520, the method determines whether the trolley 120 has reached the end of the aisle 106. If false, the method loops to 494. Otherwise, at 522, the method resets the timer. At 524, the method determines whether the interlock condition is satisfied. If false, the method loops. If true, at 526, the method outputs the one or more control signals to the wheel drive system 152*b* to drive the one wheel 150 of the pair of wheels 150*b* to move the trolley 120 along the aisle 106 in the second direction. The method also starts the timer. The method loops to 494.

Figure 6:
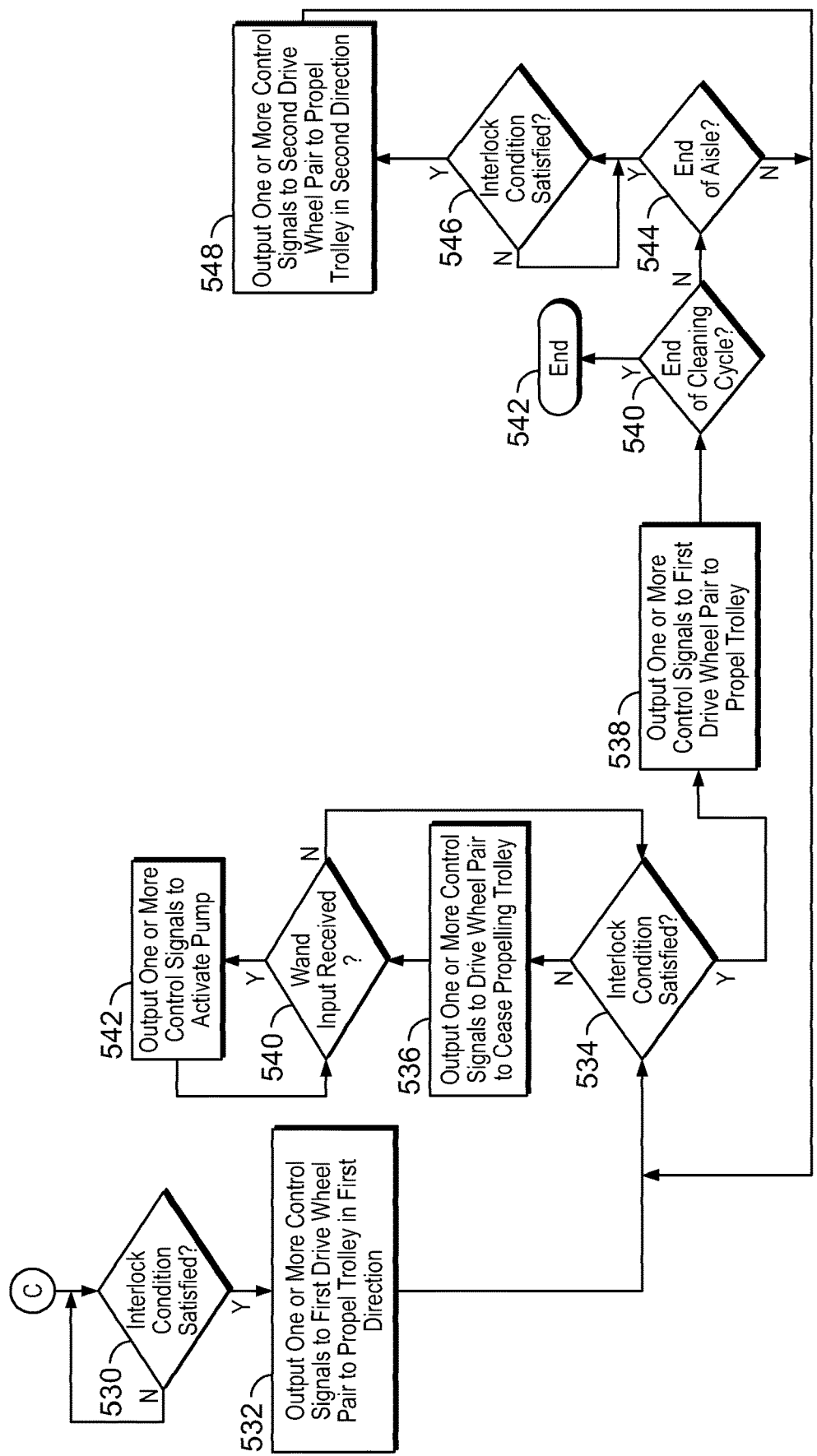

From C on FIG. 6, at 530, the method determines whether the interlock condition is satisfied or true based on the sensor signals from the interlock sensors 164. If false, the method loops. Otherwise, the method proceeds to 532. At 532, the method outputs the one or more control signals to the wheel drive system 152*a* to drive the one wheel 150 of the pair of wheels 150*a* to move the trolley 120 along the aisle 106 in the first direction. At 534, the method determines whether the interlock condition is satisfied or true based on the sensor signals from the interlock sensors 164. If false, the method proceeds to 536. Otherwise, the method proceeds to 538. At 536, the method outputs one or more control signals to stop the respective wheel drive system 152*a*, 152*b* to inhibit or halt the movement of the trolley 120. At 540, the method determines whether input has been received to the trigger 178*a* of the spray wand 178 based on the signals from the trigger 178*a*. If true, the method proceeds to 542. Otherwise, the method loops to 534. At 542, the method outputs one or more control signals to the pump 172 to activate the pump 172 to dispense the liquid disinfectant through the spray wand 178.

At 534, if the interlock condition is satisfied or true, the method proceeds to 538. At 538, the method outputs the one or more control signals to the respective wheel drive system 152a, 152b to drive the one wheel 150 of the pair of wheels 150a, 150b to move the trolley 120 along the aisle 106. At 540, the method determines whether it is the end of the cleaning cycle or determines the cycle data 353. If true, at 542, the method ends. The method may also determine the dosage data 378 for the liquid dispensed, and output the dosage data 378 to the other entities 180 and/or the display 184. Otherwise, if false, at 544, the method determines whether the trolley 120 has reached the end of the aisle 106. If false, the method loops to 534. Otherwise, at 546, the method determines whether the interlock condition is satisfied. If false, the method loops. If true, at 548, the method outputs the one or more control signals to the wheel drive system 152b to drive the one wheel 150 of the pair of wheels 150b to move the trolley 120 along the aisle 106 in the second direction. The method loops to 534.

It should be noted that while the mobile sanitization system 100 is described herein as being used to sanitize, clean or disinfect the surfaces of the mobile platform 102, a mobile sanitization system may be configured differently. In this regard, with reference to FIG. 7, a mobile sanitization system 600 is shown. As the mobile sanitization system 600 includes the same or similar components as the mobile sanitization system 100 discussed with regard to FIGS. 1-6, the same reference numerals will be used. In this example, the mobile sanitization system 600 includes a movable trolley 620 and the two extendable arms 122a, 122b. The trolley 620 includes a housing 624, one or more sensors 628, the disinfectant system 130, the power source 132, the communication system 134, the human-machine interface (HMI) 136 and a controller 638. The trolley 620 may also include the arm drive system 140, which is coupled to the extendable arms 122a, 122b to move the extendable arms 122a, 122b relative to the trolley 620.

Figure 7:
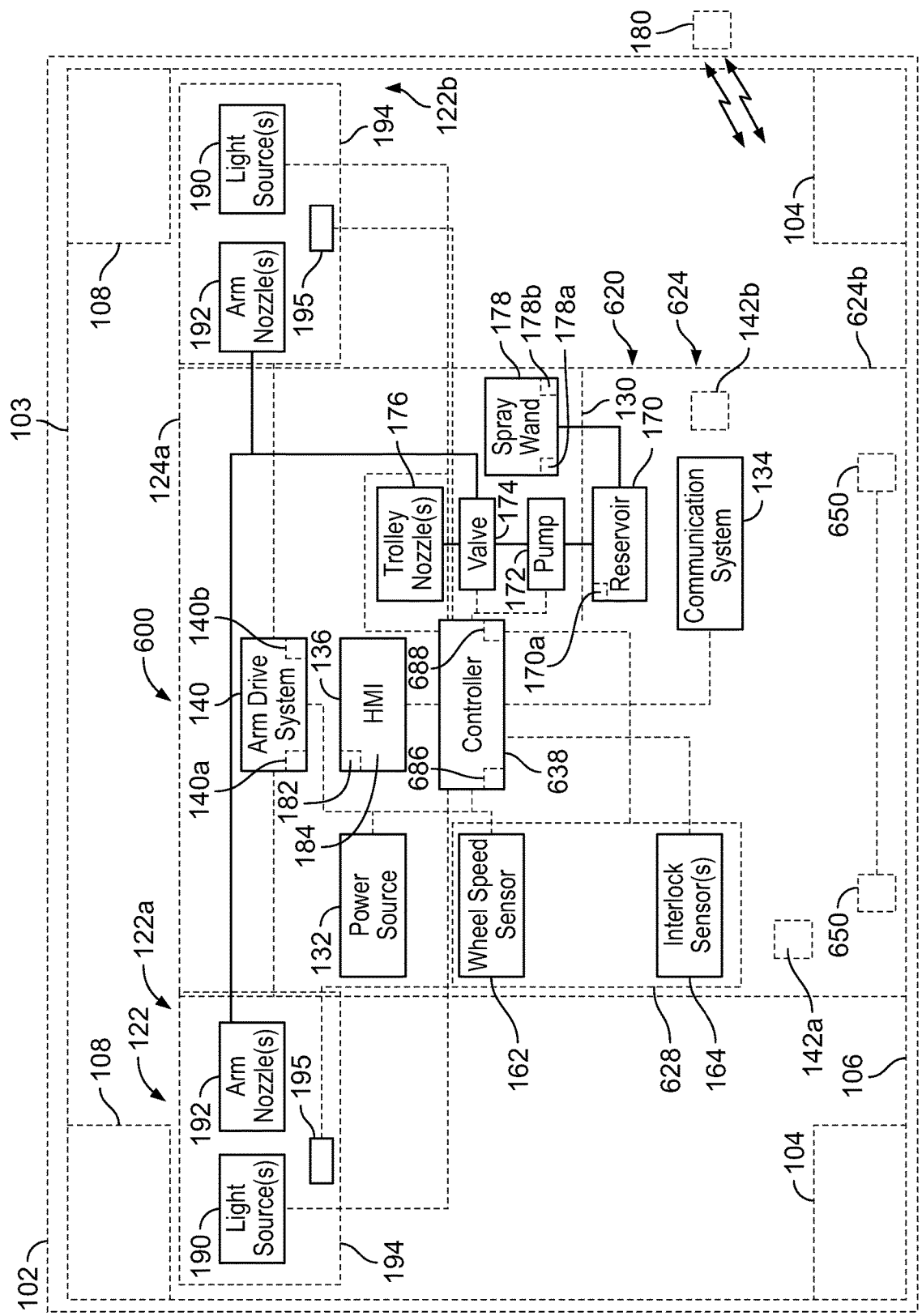
FIG. 7 is a functional block diagram of another exemplary mobile sanitization system in accordance with the various teachings of the present disclosure.

The housing 624 supports the extendable arms 122a, 122b on opposed sides of the housing 624. The housing 624 may be any suitable shape for traversing the aisles 106, and in one example, is generally rectangular. The housing 624 may be composed of any suitable material, including, but not limited to, metal, metal alloy, a polymer-based material, etc. In one example, the housing 624 may include an internal support structure or frame, which is enclosed by one or more panels. The panels may be composed of a material that is different than the frame. The housing 624 includes the two handles 142a, 142b. The handles 142a, 142b are coupled to opposed sides of the housing 624 so as to face opposed ends of the aisle 106. It should be noted that the location of the handles 142a, 142b in FIG. 7 is merely an example, as generally, the handles 142a, 142b are positioned on the housing 624 at a location that enables the operator to grasp the respective handle 142a, 142b as the mobile sanitization system 600 is moved down the aisle 106. Each of the handles 142a, 142b is coupled to one of the one or more sensors 628, as will be discussed. In this example, the housing 624 includes one or more wheels 650. The one or more wheels 650 enable the operator to push or pull the trolley 620 down the aisle 106. In one example, although two wheels 650 are shown in FIG. 7 for ease of illustration, generally, the trolley 620 includes four wheels 650, which are coupled proximate corners of the housing 624. The wheels 650 are supported for rotation on the housing 624 via a pair of shafts rotatable relative to the frame, for example. Thus, in this example, the mobile sanitization system 600 is not self-propelled, but rather, is advanced along the aisle 106 by the operator to sanitize the surfaces in the cabin 103.

The one or more sensors 628 are in communication with the controller 638 over a suitable communication architecture that supports the transfer of data and power, including, but not limited to a bus. In one example, the one or more sensors 628 include the wheel speed sensor 162 and the one or more interlock sensors 164. The wheel speed sensor 162 observes a rate of rotation of one of the wheels 650, and generates sensor signals based on the observation, which are communicated to the controller 638. In one example, one of the wheels 650 includes a marking, such as a painted line, etc., and the wheel speed sensor 162 is a camera that observes the marking to determine a speed of the wheel 650 (based on a time between observations of the marking, for example). In other examples, the wheel speed sensor 162 may comprise a Hall effect sensor, which observes a toothed ring coupled to shaft that interconnects the wheels 650. Thus, generally, the wheel speed sensor 162 is any suitable sensor that directly or indirectly observes an amount of rotation of the wheel 650 and outputs sensor signals to the controller 638.

In this example, the sensors 628 includes two of the interlock sensors 164, which are associated with a respective one of the handles 142a, 142b. In one example, a respective one of the interlock sensors 164 is coupled to the handle 142a, and the other of the interlock sensors 164 is coupled to the handle 142b. As discussed, the interlock sensors 164 observe whether a hand of an operator is positioned about or coupled to the respective handle 142a, 142b, and outputs sensor signals to the controller 638 based on the observation.

As discussed, the disinfectant system 130 includes the reservoir 170, the pump 172, the valve 174, the one or more trolley nozzles 176 and the spray wand 178. The reservoir 170 includes the level sensor 170a. The pump 172 is fluidly coupled to the reservoir 170 via one or more hoses, quick connect couplings and the like, for example, to draw the liquid disinfectant from the reservoir 170. The valve 174 is fluidly coupled between the pump 172, the trolley nozzles 176 and the arm nozzles 192 via respective hoses, quick connect couplings and the like, for example, to control a flow of the liquid disinfectant from the pump 172 to the trolley nozzles 176 and the arm nozzles 192. The trolley nozzles 176 are coupled to the housing 624 of the trolley 620 via one or more mechanical fasteners, for example. Generally, the housing 624 includes a first, top end 624a opposite a second, bottom end 624b. In one example, the trolley nozzles 176 are coupled to the housing 624 at or near the bottom end 624b. By coupling the trolley nozzles 176 at or near the bottom end 624b of the housing 624, the trolley nozzles 176 may spray the liquid disinfectant along a floor of the aisle 106. In addition, the trolley nozzles 176 may be arranged about a perimeter or on the sides of the housing 624 such that the trolley nozzles 176 may spray the liquid disinfectant under the passenger seats 104 as the mobile sanitization system 600 moves along the aisle 106. It should be noted that a manifold may be coupled between the valve 174 and the trolley nozzles 176 to assist in directing the liquid disinfectant from the valve 174 to each of the trolley nozzles 176. In one example, the trolley 620 may include one to about four trolley nozzles 176 coupled to the housing 624 about the perimeter of the housing 624 at or near the bottom end 624b. It should be noted, that if desired, one or more of the trolley nozzles 176 may be coupled to the housing 624 at other locations along the trolley 620. For example, trolley nozzles 176 may be coupled at or near the top end 624a to assist in cleaning the stowage compartments 108. The trolley nozzles 176 may also be coupled between the top end 624a and the bottom end 624b to assist in cleaning sides of the passenger seats 104 that line the aisle 106. Also, in certain instances, a portion of the housing 624 of the trolley 620 may be extendable relative to a fixed portion of the trolley 620 (to raise or lower a height of the arms 122a, 122b relative to the floor of the aisle 106, for example), and one or more of the trolley nozzles 176 may be coupled to the housing 624 so as to be movable with the portion of the housing 624, if desired. The controller 638 may receive input to move the movable portion of the housing 624 relative to the fixed portion via the human-machine interface 136, for example.

The spray wand 178 is fluidly coupled to the pump 172 via one or more hoses, quick connect couplings and the like, for example. The spray wand 178 may also be coupled to or retained on the housing 624 of the trolley 620 by a receptacle, U-shaped holder coupled to the housing 624 or other retaining device configured to retain the spray wand 178. The spray wand 178 includes the trigger 178a that is manipulatable by an operator to dispense the liquid disinfectant through the nozzle 178b associated with the spray wand 178. In one example, the trigger 178a of the spray wand 178 is in communication with the controller 638, over a suitable communication architecture that supports the transfer of data and power, including, but not limited to a bus, such that a manipulation, such as a pulling, of the trigger 178a sends a signal to the controller 638. It should be noted that the spray wand 178 is merely one example, as a spray wand associated with the trolley 620 need not be in communication with the controller 638, but rather, the pump 172 may run continuously during an operation of the mobile sanitization system 600 such that a manipulation of a trigger of the spray wand dispenses the liquid disinfectant. The spray wand 178 is removable from the trolley 620 by the operator to dispense the liquid disinfectant to disinfect a targeted area of the surfaces of the cabin 103. For example, the spray wand 178 may be used to disinfect surfaces that are not easily disinfected by one or more light sources 190, the trolley nozzles 176 and/or one or more arm nozzles 192, including, but not limited to handles of the stowage compartments 108, directly underneath the passenger seats 104, seat belt buckles, corners of galleys, corners of lavatories, etc. It should be noted, however, that due to the spray wand 178, the trolley 620 may complete a cleaning cycle in a single pass or movement down the aisle 106 such that a return pass is not necessary. Thus, although the cleaning cycle is described herein as a movement of the trolley up and down the aisle 106, the cleaning cycle may be completed in a single trip down the aisle 106.

The power source 132 supplies power to the mobile sanitization system 600. The power source 132 is in communication with the controller 638 via a suitable communication architecture that supports the transfer of data and power, including, but not limited to a bus. The communication system 134 is configured to wirelessly communicate information to and from the other entities 180. The communication system 134 and the human-machine interface 136 are each in communication with the controller 638 via a suitable communication architecture that supports the transfer of data and power, including, but not limited to a bus. The human-machine interface 136 may include various switches, dials, levers, one or more buttons, the touchscreen interface 182 that may be overlaid on the display 184, a keyboard, an audible device, a microphone associated with a speech recognition system, the trigger 178a of the spray wand 178, or various other human-machine interface devices. The human-machine interface 136 is coupled to the housing 624. In certain instances, the human-machine interface 136 may be removable from the housing 624. In this example, the display 184 is an electronic display capable of graphically displaying one or more user interfaces under the control of the controller 638. Those skilled in the art may realize other techniques to implement the display 184 on the trolley 620.

The controller 638 includes at least one processor 686 and a computer-readable storage device or media 688. The processor 686 may be any custom-made or commercially available processor, a central processing unit (CPU), a graphics processing unit (GPU), an application specific integrated circuit (ASIC) (e.g., a custom ASIC implementing a neural network), a field programmable gate array (FPGA), an auxiliary processor among several processors associated with the controller 638, a semiconductor-based microprocessor (in the form of a microchip or chip set), any combination thereof, or generally any device for executing instructions. The computer readable storage device or media 688 may include volatile and nonvolatile storage in read-only memory (ROM), random-access memory (RAM), and keep-alive memory (KAM), for example. KAM is a persistent or non-volatile memory that may be used to store various operating variables while the processor 186 is powered down. The computer-readable storage device or media 188 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 638 in controlling the mobile sanitization system 600. In various embodiments, the controller 638 is configured to implement instructions of the sanitization control system 700 as discussed in detail below.

In various embodiments, the instructions, when executed by the processor 686, receive and process input data received from the human-machine interface 136 to disinfect and sanitize the surfaces associated with the mobile platform 102 as the mobile sanitization system 600 travels along the aisle 106. The instructions determine whether it is selected to use at least one of the light sources 190, the nozzles (the trolley nozzles 176 and the arm nozzles 192) and the spray wand 178 to disinfect and sanitize the surfaces associated with the mobile platform 102 and controls the mobile sanitization system 600 to travel along the aisle 106 based on the selection.

The trolley 620 includes the arm drive system 140. The arm drive system 140 may comprise any suitable electromechanical system configured to move the extendable arms 122a, 122b from the first position, in which the arms 122a, 122b are in the collapsed state within the trolley 620 so as to be contained within a footprint defined by the housing 624 of the trolley 620, to the second position, in which the arms 122a, 122b are extended outwardly away from the trolley 620 and suspended above the surfaces of the passenger seats 104 and below the surfaces of the stowage compartments 108. In one example, the arm drive system 140 includes two linear actuators 140a, 140b that are responsive to control signals from the controller 638 to move the arms 122a, 122b relative to the trolley 120. The linear actuators 140a, 140b are each in communication with the controller 638 over a suitable communication architecture that supports the transfer of data and power, including, but not limited to a bus.

As discussed, the extendable arms 122a, 122b are movably coupled to the trolley 620. In one example, each of the extendable arms 122a, 122b include the one or more light sources 190, the one or more arm nozzles 192 and the one or more arm proximity sensors 195. The light sources 190, the arm nozzles 192 and the arm proximity sensors 195 are supported on the respective arm support structure 194. In one example, each of the arm support structures 194 comprises a horizontal scissors mechanism, which is coupled to the respective one of the linear actuators 140a, 140b and to the housing 624. Each of the light sources 190 and the arm proximity sensors 195 are in communication with the controller 638 over a suitable communication architecture that supports the transfer of data and power, including, but not limited to a bus. The arm nozzles 192 are coupled to the arm support structure 194 to extend along a perimeter of the arm support structure 194 via one or more mechanical fasteners, for example. Each of the arm nozzles 192 is fluidly coupled to the valve 174 via a respective hose, fluid coupling, etc.

Figure 8:
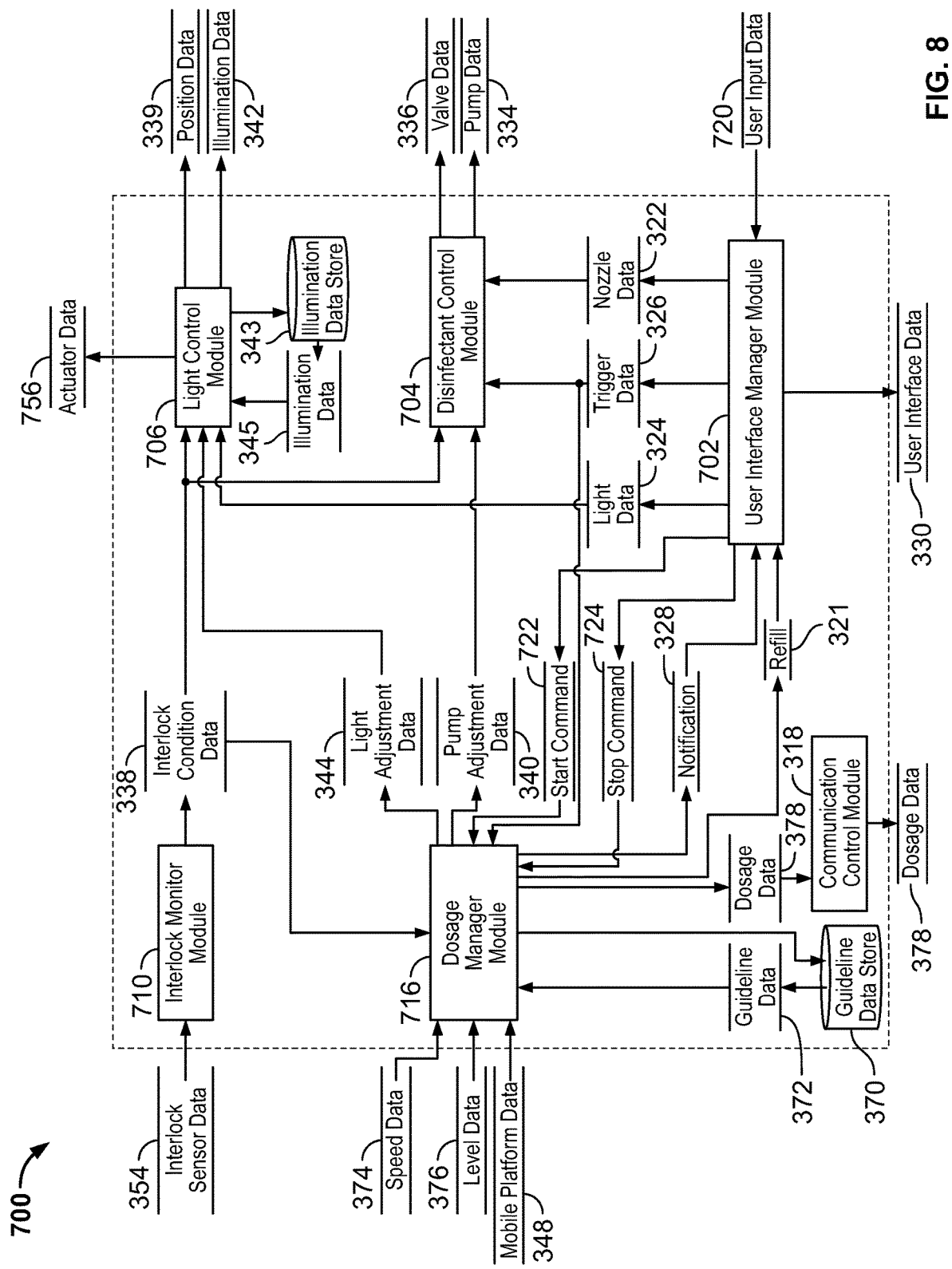
FIG. 8 is a dataflow diagram illustrating a sanitization control system for the mobile sanitization system of FIG. 7 in accordance with various embodiments.
Figure 9:
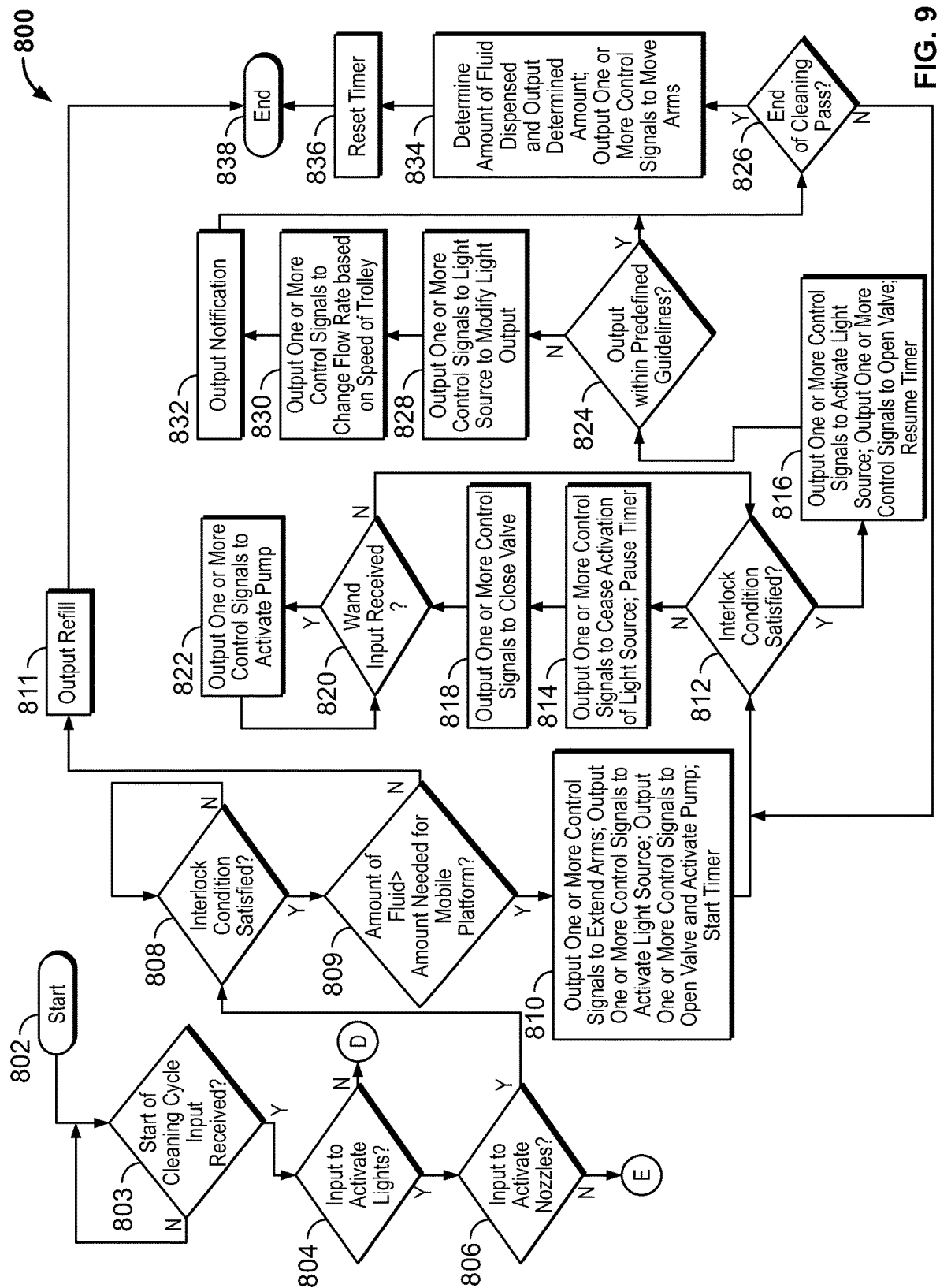
FIGS. 9-12 are flowcharts illustrating a control method that can be performed by the sanitization control system of FIG. 8 in accordance with various embodiments.

With reference now to FIG. 8 and with continued reference to FIG. 7, FIG. 8 is a dataflow diagram illustrating aspects of the sanitization control system 700 for the mobile sanitization system 600, which is embedded within the controller 638. As can be appreciated, the modules and sub-modules shown in FIG. 8 can be combined and/or further partitioned to similarly perform the functions described herein. Inputs to modules and sub-modules may be received from the sensors 628, received from other control modules (not shown) associated with the mobile sanitization system 600, received from the human-machine interface 136, received from the communication system 134, received from the trigger 178a and/or determined/modeled by other sub-modules (not shown) within the controller 638 of FIG. 1. The modules and sub-modules shown generally perform the functions of controlling the mobile sanitization system 600 to disinfect or sanitize the mobile platform 102. As shown in FIG. 8, the sanitization control system 700 includes a user interface (UI) manager module 702, a disinfectant control module 704, a light control module 706, an interlock monitor module 710, a dosage manager module 716 and the communication control module 318.

The UI manager module 702 receives as input the user input data 720 from the human-machine interface 136. The UI manager module 702 processes the user input data 720 and determines whether input has been received to start a cleaning cycle. If true, the UI manager module 702 sets start command 722 for the dosage manager module 716. The UI manager module 702 also processes the user input data 720 and determines whether input has been received to end a cleaning cycle. If true, the UI manager module 702 sets stop command 724 for the dosage manager module 716. The UI manager module 702 processes the user input data 720 and determines whether input has been received to activate the trolley nozzles 176 and the arm nozzles 192. If true, the UI manager module 702 sets nozzle data 322 for the disinfectant control module 704. The UI manager module 702 also processes the user input data 720 to determine whether input has been received to activate the light sources 190. If true, the UI manager module 702 sets light data 324 for the light control module 706. The UI manager module 702 also processes the user input data 720 to determine whether input has been received to the trigger 178a to activate the spray wand 178. If true, the UI manager module 702 sets trigger data 326 for the disinfectant control module 704 and the dosage manager module 716. The trigger data 326 indicates that a request to activate the spray wand 178 has been received via input to the trigger 178a.

The UI manager module 702 also receives as input the notification 328. Upon receipt of the notification 328, the UI manager module 702 generates and outputs the user interface data 330 for rendering the user interface on the display 184 associated with the human-machine interface 136. The UI manager module 702 may optionally receive as input dosage data 332 from the dosage manager module 316. The UI manager module 702 may also generate and output the user interface data 330 for rendering the user interface on the display 184, which includes the dosage data 332.

The UI manager module 702 also receives as input refill 321. The refill 321 indicates that additional liquid disinfectant is needed in the reservoir 170 prior to the beginning of a cleaning cycle. Upon receipt of the refill 321, the UI manager module 702 generates and outputs the user interface data 330 for rendering the user interface on the display 184 associated with the human-machine interface 136. The user interface data 330 may comprise the user interface with text and/or graphics that indicate that additional fluid is needed in the reservoir 170.

The disinfectant control module 704 receives as input the interlock condition data 338 from the interlock monitor module 710 and the nozzle data 322. If the interlock condition data 338 indicates true or that the interlock condition is satisfied, based on the nozzle data 322, the disinfectant control module 704 outputs the pump data 334 and the valve data 336. Generally, the valve 174 is in the second, closed position at a start-up of the mobile sanitization system 600 such that the valve data 336 moves the valve 174 from the second, closed position to the first, opened position.

The disinfectant control module 704 also receives as input trigger data 326. Based on the trigger data 326, the disinfectant control module 704 sets the pump data 334 for the pump 172. The disinfectant control module 704 receives as input the pump adjustment data 340 from the dosage manager module 716. The pump adjustment data 340 indicates an adjusted flow rate for the pump 172 to adjust the output of the trolley nozzles 176 and the arm nozzles 192. Based on the receipt of the pump adjustment data 340, the disinfectant control module 704 outputs the pump data 334 to the pump 172 for the pump 172 to operate at the adjusted flow rate.

The light control module 706 receives as input the interlock condition data 338 from the interlock monitor module 710 and the light data 324. If the interlock condition data 338 indicates true or that the interlock condition is satisfied, based on the light data 324, the light control module 706 outputs actuator data 756. The actuator data 756 is one or more control signals to the linear actuators 140a, 140b of the arms 122a, 122b to activate the linear actuators 140a, 140b to move the arms 122a, 122b relative to the trolley 620 from the first position to the second position.

The light control module 706 also receives as input the position data 339. The light control module 706 processes the position data 339 and determines the distance between the respective surface of the respective arm 122a, 122b and the surface within the mobile platform 102. With the interlock condition data 338 as satisfied and the output of the actuator data 756, based on the receipt of the light data 324 and the determined position of the respective surfaces of the respective arms 122a, 122b, the light control module 706 queries the illumination datastore 343 and retrieves the illumination output data 345. Based on the retrieved illumination output data 345, the light control module 706 outputs the illumination data 342. If the interlock condition data 338 indicates false or that the interlock condition is not satisfied, the light control module 706 waits for the interlock condition data 338 to be true before outputting the illumination data 342 or ceases outputting the illumination data 342. The light control module 706 also receives as input light adjustment data 344 from the dosage manager module 316. Based on the receipt of the light adjustment data 344, the light control module 706 outputs the illumination data 342 to the light sources 190 to operate at the adjusted amount of illumination.

The interlock monitor module 710 receives as input the interlock sensor data 354. Based on the interlock sensor data 354, the interlock monitor module 710 determines whether the operator's hand is on the handle 142a, 142b and sets the interlock condition data 338 for the light control module 706 and the disinfectant control module 704 based on this determination. As discussed, the interlock condition data 338 is true if the interlock monitor module 710 determines based on the interlock sensor data 354 that the operator's hand is on one of the handles 142a, 142b; and the interlock condition data 338 is false if the interlock monitor module 710 determines based on the interlock sensor data 354 that the operator's hand is not on the handles 142a, 142b.

The guidelines datastore 370 stores one or more look-up tables that provide, for a particular mobile platform 102, the amount of illumination for the light sources 190 and the flow rate for the pump 172 based on a particular rate of travel of the trolley 620 along the aisle 106. Thus, the one or more look-up tables store guideline data 372 indicating the amount of illumination for the light sources 190 and the flow rate for the pump 172 based on a rate of travel the trolley 620 to sanitize the surfaces along a particular aisle 106 of the particular mobile platform 102 as discussed.

The dosage manager module 716 receives as input the mobile platform data 348, the speed data 374 and the level data 376. The dosage manager module 716 also receives as input the start command 722 and the stop command 724. Based on the start command 722 and the level data 276, the dosage manager module 716 determines the amount of fluid remaining in the reservoir 170. The dosage manager module 716 determines, based on the mobile platform data 348, whether the amount of fluid remaining in the reservoir 170 is sufficient to complete a cleaning cycle. Stated another way, the dosage manager module 716 compares the amount of fluid in the reservoir 170 from the level sensor 170a to an amount of fluid required to clean the mobile platform 100 from the mobile platform data 348. If the amount of fluid in the reservoir 170 is less than the amount of fluid needed to clean the mobile platform 100, the dosage manager module 316 sets the refill 321 for the UI manager module 702.

Based on the receipt of the start command 722, the dosage manager module 716 also starts a timer and sets the level data 376 as an initial fluid level for the reservoir 170. The dosage manager module 716 determines a rate of travel of the trolley 620 down the aisle 106 by dividing the speed data 374 by the time recorded by the timer. Based on the mobile platform data 348 and the rate of travel, the dosage manager module 716 queries the guideline datastore 370 and retrieves the guideline data 372 associated with the mobile platform 102. The dosage manager module 716 determines based on the guideline data 372 and the rate of travel of the trolley 620, the amount of illumination for the light sources 190 and the flow rate for the pump 172. If the amount of illumination retrieved for the light sources 190 is different than a current amount of illumination for the light sources 190 (which is a stored in a memory associated with the dosage manager module 716), the dosage manager module 716 sets the light adjustment data 344 for the light control module 706 based on the difference between the current amount of illumination and the retrieved amount of illumination. If the flow rate retrieved for the pump 172 is different than a current flow rate for the pump 172 (which is stored in a memory associated with the dosage manager module 716), the dosage manager module 716 sets the pump adjustment data 340 for the disinfectant control module 704 based on the difference between the current flow rate and the retrieved flow rate. The dosage manager module 716 sets the notification 328 for the UI manager module 702. During a start-up of the trolley 620, the initial flow rate for the pump 172 is predefined or factory set, at about 1 gallon per minute to about 3 gallons per minute based on a speed of 10 rows per minute; and the illumination output by the light sources 190 is about 2.5 milliwatts (mW) to about 6 milliwatts (mW) based on a speed of 10 rows per minute.

The dosage manager module 716 receives as input the trigger data 326. Based on the trigger data 326, the dosage manager module 716 pauses the timer. The dosage manager module 716 receives as input the interlock condition data 338. If the interlock condition data 338 indicates that the interlock condition is satisfied, the dosage manager module 716 resumes the timer. The dosage manager module 716 receives as input the stop command 724. Based on the stop command 724, the dosage manager module 716 receives as input level data 376. The dosage manager module 716 determines a change in the fluid level of the reservoir 170 by subtracting the initial fluid level from the level data 376 at the end of the cleaning cycle. The dosage manager module 716 sets the difference between the initial fluid level and the fluid level as the liquid disinfectant dosage in the dosage data 378. In certain instances, the dosage manager module 716 may query a datastore and retrieve a percent disinfection based on the volume of liquid disinfectant dispensed and the given surface area of the mobile platform 102 from the mobile platform data 348 (e.g. a percent disinfection for the mobile platform 102 based on gallons per square feet dispensed). The dosage manager module 716 also determines a light dosage and includes the determined light dosage as dosage data 378. The light dosage is determined based on pre-set factory values that provide a percent reduction in a microbial amount (e.g. bacteria colonies) as a function of time for a given illumination output (light energy). Based on the time of the illumination of the light sources 190 and the illumination output by the light sources 190, the dosage manager module 716 determines the light dosage as the percent reduction in a microbial amount based on the pre-set factory values. For example, the dosage manager module 716 may query a datastore that stores a look-up table, which provides the light dosage or percent reduction in a microbial amount for a particular time of illumination and a particular illumination output by the light sources 190. Thus, generally, the dosage data 378 includes at least one of the amount of liquid disinfectant dispensed by the trolley nozzles 176, the arm nozzles 192 and the spray wand 178, and the percent reduction in a microbial amount from the light output by the light sources 190 at the end of a cleaning of the aisle 106.

The communication control module 318 receives as input the dosage data 378. Based on the receipt of the dosage data 378, the communication control module 318 outputs the dosage data 378 for communication to the other entities 180 via the communication system 134. In certain examples, the communication control module 318 may also receive as input data from the other entities 180 such as one or more commands to control the mobile sanitization system 600. For example, the light data 324 and the nozzle data 322 may be received as input from the other entities 180 via the communication control module 318, which may set the light data 324 and the nozzle data 322 for the light control module 706 and the disinfectant control module 704, respectively.

With reference now to FIGS. 9-12, and continued reference to FIGS. 7 and 8, a flowchart illustrates a control method 800 that may be performed by the sanitization control system 700 in accordance with various embodiments. In various embodiments, the control method 800 is performed by the processor 686 of the controller 638. As can be appreciated in light of the disclosure, the order of operation within the method is not limited to the sequential execution as illustrated in FIGS. 9-12 but may be performed in one or more varying orders as applicable and in accordance with the present disclosure. In various embodiments, the control method 800 can be scheduled to run based on one or more predetermined events, such as based upon receipt of the user input data 320.

The method begins at 802. At 803, the method determines whether input has been received, via the user input data 720, to start a cleaning cycle. If false, the method loops. If true, at 804, the method determines whether user input data 720 has been received to activate the light sources 190. If true, the method proceeds to 806. Otherwise, the method proceeds to D on FIG. 10. At 806, the method determines whether user input data 720 has been received to activate the trolley nozzles 176 and the arm nozzles 192. If true, the method proceeds to 808. Otherwise, the method proceeds to E on FIG. 11.

At 808, the method determines whether the interlock condition is satisfied or true based on the sensor signals from the interlock sensors 164. If false or unsatisfied, the method loops. Otherwise, at 810, the method determines the initial fluid level of the reservoir 170, and determines whether the initial fluid level is greater than the amount of fluid needed to complete a cleaning cycle or to disinfect the mobile platform based on the mobile platform data 348. If true, the method proceeds to 810. Otherwise, at 811, the method outputs the user interface data 330 that indicates that a refill of the reservoir 170 is needed to complete the cleaning cycle. The method ends at 838.

At 810, the method outputs one or more control signals to the linear actuators 140*a*, 140*b* to extend the arms 122*a*, 122*b*. The method also receives the sensor signals from the arm proximity sensors 195 and determines the distance between the respective surface of the respective arm 122*a*, 122*b* and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method also outputs one or more control signals to open the valve 174, and outputs one or more control signals to activate the pump 172. The method starts the timer.

At 812, the method determines whether the interlock condition is satisfied or true based on the sensor signals from the interlock sensors 164. If false, the method proceeds to 814. Otherwise, the method proceeds to 816.

At 814, the method ceases outputting the one or more control signals to the light sources 190 such that the light sources 190 are deactivated or are no longer illuminated. The method pauses the timer. At 818, the method outputs the one or more control signals to the valve 174 to move the valve 174 from the current position (first, opened position) to the opposite position (second, closed position). At 820, the method determines whether input has been received to the trigger 178*a* of the spray wand 178 based on the signals from the trigger 178*a*. If true, the method proceeds to 822. Otherwise, the method loops to 812. At 820, the method outputs one or more control signals to the pump 172 to activate the pump 172 to dispense the liquid disinfectant through the spray wand 178.

At 812, if the interlock condition is satisfied or true, the method proceeds to 816. At 816, the method receives the sensor signals from the arm proximity sensors 195 and determines the distance between the respective surface of the respective arm 122*a*, 122*b* and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method determines whether the valve 174 is in the first, opened position, and if not, the method outputs the one or more control signals to the valve 174 to move the valve 174 to the first, opened position based on the position of the valve 174 received from the position sensor associated with the valve 174, for example. The method resumes the timer. At 824, the method determines whether the amount of light output by the light sources 190 and the amount of liquid disinfectant output by the pump 172 is within predefined guidelines based on the rate of travel of the trolley 620, the particular mobile platform 102 and the guideline data 372 retrieved from the guideline datastore 370. If true, the method proceeds to 826.

Otherwise, at 828, the method outputs one or more control signals to the light sources 190 based on the modified amount of illumination of the light sources 190 from the light adjustment data 344. At 830, the method outputs one or more control signals to the pump 172 based on the modified flow rate of the pump 172 from the pump adjustment data 346. At 832, the method outputs the user interface data 330 to render the user interface including the notification on the display 184. For example, the user interface including the notification may textually or graphically indicate that the amount of illumination of the light sources 190 and the flow rate of the pump 172 has been modified to account for the rate of travel of the trolley 620.

At 826, the method determines whether it is the end of the cleaning cycle. In this regard, the method determines whether user input data 720 has been received to end the cleaning cycle. If true, at 834, the method determines the amount of fluid dispensed by the trolley nozzles 176, the spray wand 178 and the arm nozzles 192 based on a difference between the initial fluid level value and the end fluid level value of the reservoir 170. The method determines the dosage data 378 for the light output by the light sources 190 and the amount of liquid dispensed by the trolley nozzles 176, the spray wand 178 and the arm nozzles 192, and outputs the dosage data 378 to the other entities 180 and/or the display 184. The method resets the timer to zero and outputs one or more control signals to the linear actuators 140*a*, 140*b* to move the arms 122*a*, 122*b* from the second position to the first position at 836 and ends at 838. Otherwise, if false at 826, the method loops to 812.

Figure 10:
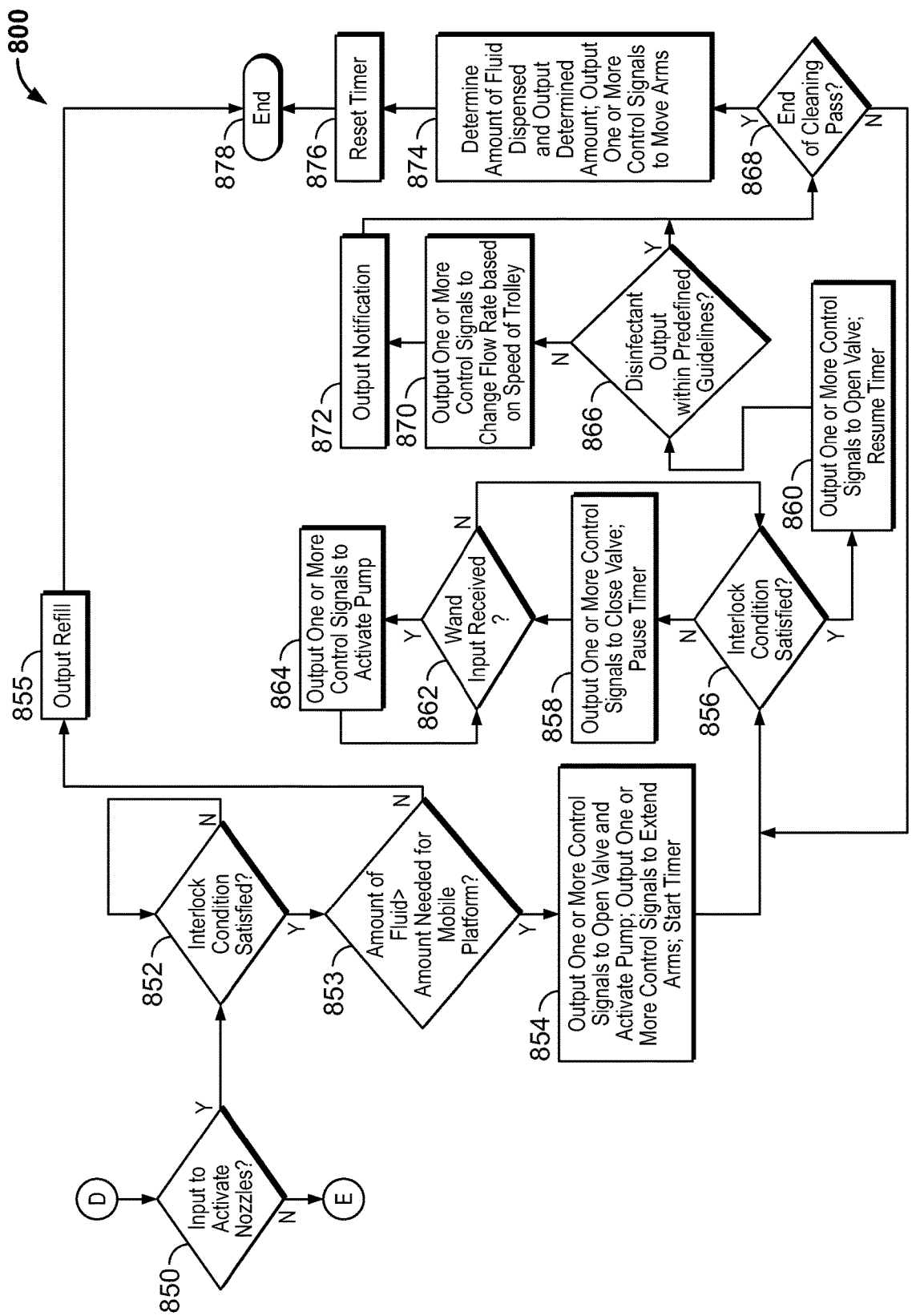

From D on FIG. 10, the method determines at 850 whether user input data 320 has been received to activate the trolley nozzles 176 and the arm nozzles 192. If true, the method proceeds to 852. Otherwise, the method proceeds to F on FIG. 12.

At 852, the method determines whether the interlock condition is satisfied or true based on the sensor signals from the interlock sensors 164. If false, the method loops. Otherwise, at 853, the method determines the initial fluid level of the reservoir 170, and determines whether the initial fluid level is greater than the amount of fluid needed to complete a cleaning cycle or to disinfect the mobile platform based on the mobile platform data 348. If true, the method proceeds to 854. Otherwise, at 855, the method outputs the user interface data 330 that includes the user interface that indicates that a refill of the reservoir 170 is needed to complete the cleaning cycle. The method ends at 878.

At 854, the method outputs one or more control signals to the linear actuators 140a, 140b to extend the arms 122a, 122b or to move the arms 122a, 122b from the first position to the second position. The method also outputs one or more control signals to open the valve 174, and outputs one or more control signals to activate the pump 172. The method starts the timer.

At 856, the method determines whether the interlock condition is satisfied or true based on the sensor signals from the interlock sensors 164. If false, the method proceeds to 858. Otherwise, the method proceeds to 860.

At 858, the method outputs the one or more control signals to the valve 174 to move the valve 174 from the current position (first, opened position) to the opposite position (second, closed position). At 862, the method determines whether input has been received to the trigger 178a of the spray wand 178 based on the signals from the trigger 178a. If true, the method proceeds to 864. Otherwise, the method loops to 856. At 864, the method outputs one or more control signals to the pump 172 to activate the pump 172 to dispense the liquid disinfectant through the spray wand 178.

At 856, if the interlock condition is satisfied or true, the method proceeds to 860. At 860, the method determines whether the valve 174 is in the first, opened position, and if not, the method outputs the one or more control signals to the valve 174 to move the valve 174 to the first, opened position. The method resumes the timer. At 866, the method determines whether the amount of liquid disinfectant output by the pump 172 is within predefined guidelines based on the rate of travel of the trolley 620, the particular mobile platform 102 and the guideline data 372 retrieved from the guideline datastore 370. If true, the method proceeds to 868.

Otherwise, at 870, the method outputs one or more control signals to the pump 172 based on the modified flow rate of the pump 172 from the pump adjustment data 346. At 872, the method outputs the user interface data 330 to render the user interface including the notification on the display 184. For example, the user interface including the notification may textually or graphically indicate that the flow rate of the pump 172 has been modified to account for the rate of travel of the trolley 620.

At 868, the method determines whether it is the end of the cleaning cycle. In this regard, the method determines whether user input data 720 has been received to end the cleaning cycle. If true, at 874, the method determines the amount of fluid dispensed by the trolley nozzles 176, the spray wand 178 and the arm nozzles 192 based on a difference between the initial fluid level value and the end fluid level value of the reservoir 170. The method determines the dosage data 378 for amount of liquid dispensed by the trolley nozzles 176, the spray wand 178 and the arm nozzles 192, and outputs the dosage data 378 to the other entities 180 and/or the display 184. The method resets the timer to zero and outputs one or more control signals to the linear actuators 140a, 140b to move the arms 122a, 122b from the second position to the first position at 876 and ends at 878. Otherwise, if false at 868, the method loops to 856.

Figure 11:
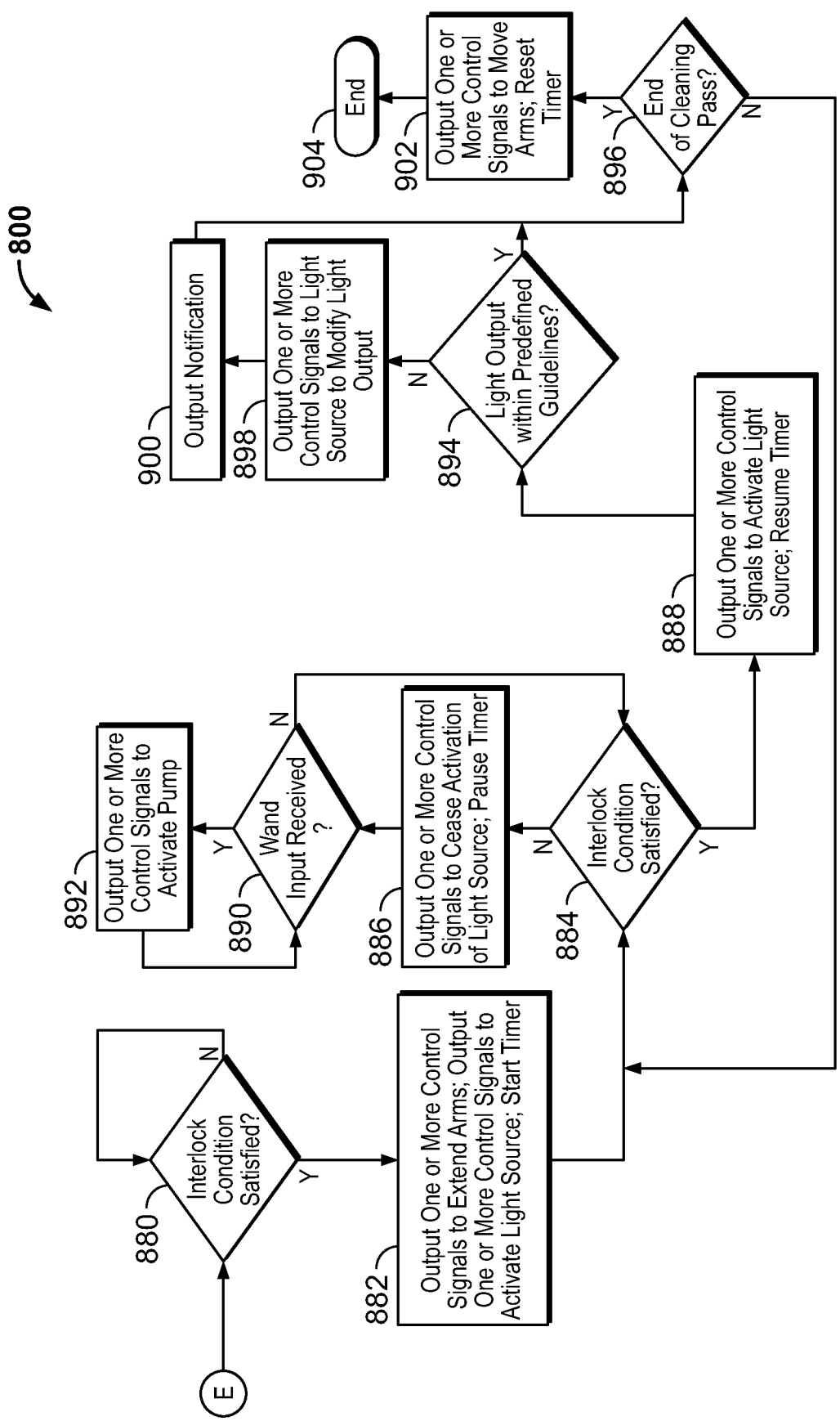

From E on FIG. 11, at 880, the method determines whether the interlock condition is satisfied or true based on the sensor signals from the interlock sensors 164. If false, the method loops. Otherwise, at 882, the method outputs one or more control signals to the linear actuators 140a, 140b to extend the arms 122a, 122b. The method also receives the sensor signals from the arm proximity sensors 195 and determines the distance between the respective surface of the respective arm 122a, 122b and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method starts the timer.

At 884, the method determines whether the interlock condition is satisfied or true based on the sensor signals from the interlock sensors 164. If false or unsatisfied, the method proceeds to 886. Otherwise, the method proceeds to 888.

At 886, the method ceases outputting the one or more control signals to the light sources 190 such that the light sources 190 are deactivated or are no longer illuminated. The method pauses the timer. At 890, the method determines whether input has been received to the trigger 178a of the spray wand 178 based on the signals from the trigger 178a. If true, the method proceeds to 892. Otherwise, the method loops to 884. At 892, the method outputs one or more control signals to the pump 172 to activate the pump 172 to dispense the liquid disinfectant through the spray wand 178.

At 884, if the interlock condition is satisfied or true, the method proceeds to 888. At 888, the method receives the sensor signals from the arm proximity sensors 195 and determines the distance between the respective surface of the respective arm 122a, 122b and the surface within the mobile platform 102. Based on the determined distances, the method retrieves the illumination output data 345 from the illumination datastore 343, and outputs one or more control signals to the light sources 190 to activate the light sources 190 to illuminate based on the illumination output data 345. The method resumes the timer. At 894, the method determines whether the amount of light output by the light sources 190 is within predefined guidelines based on the rate of travel of the trolley 620, the particular mobile platform 102 and the guideline data 372 retrieved from the guideline datastore 370. If true, the method proceeds to 896.

Otherwise, at 898, the method outputs one or more control signals to the light sources 190 based on the modified amount of illumination of the light sources 190. At 900, the method outputs the user interface data 330 to render the user interface including the notification on the display 184. For example, the user interface including the notification may textually or graphically indicate that the amount of illumination of the light sources 190 has been modified to account for the rate of travel of the trolley 620. At 896, the method determines whether it is the end of the cleaning cycle. In this regard, the method determines whether user input data 720 has been received to end the cleaning cycle. If true, at 902, the method resets the timer to zero, determines the dosage data 378 for the light output by the light sources 190, outputs the dosage data 378 to the other entities 180 and/or the display 184, outputs one or more control signals to the linear actuators 140a, 140b to move the arms 122a, 122b from the second position to the first position and ends at 904. Otherwise, if false at 896, the method loops to 884.

Figure 12:
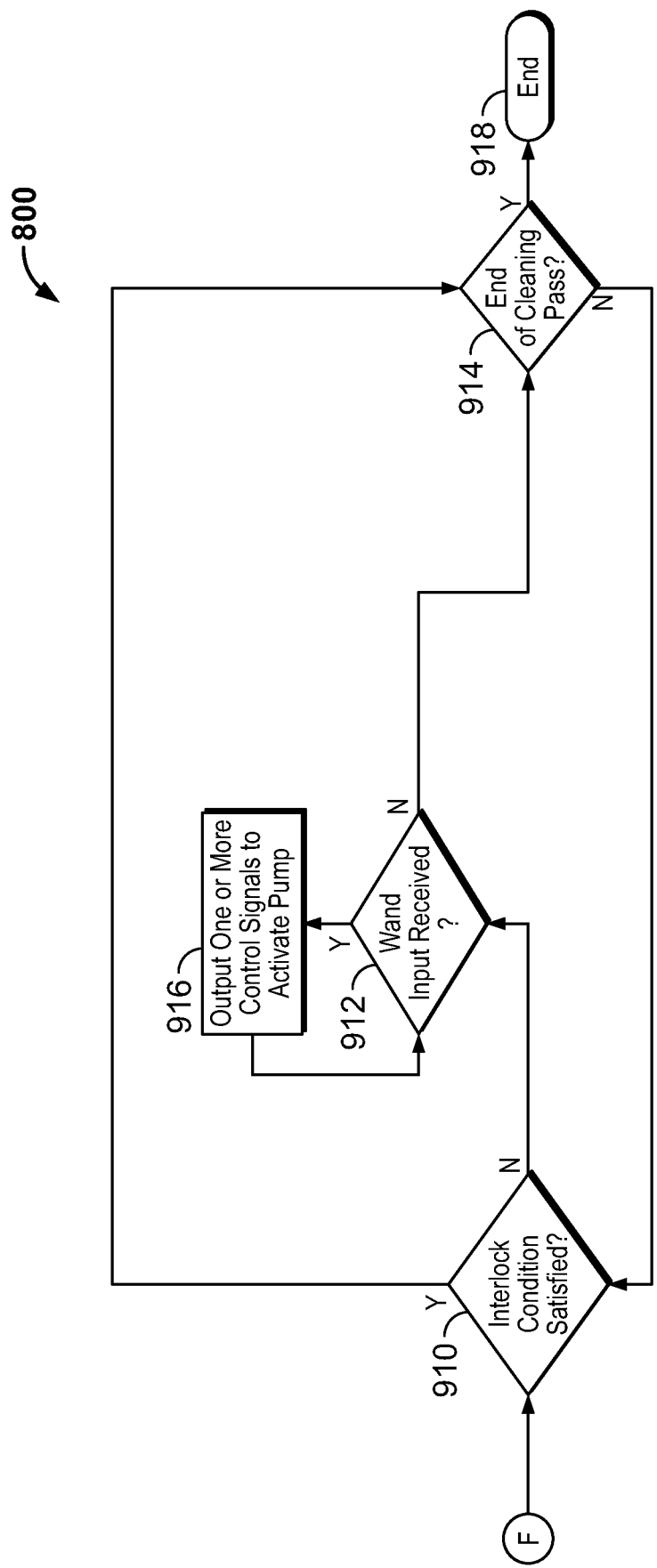

From F on FIG. 12, the method determines at 910 whether the interlock condition is satisfied or true based on the sensor signals from the interlock sensors 164. If false, the method proceeds to 912. Otherwise, the method proceeds to 914. At 912, the method determines whether input has been received to the trigger 178a of the spray wand 178 based on the signals from the trigger 178a. If true, the method proceeds to 916. Otherwise, the method proceeds to 914. At 916, the method outputs one or more control signals to the pump 172 to activate the pump 172 to dispense the liquid disinfectant through the spray wand 178.

At 910, if the interlock condition is satisfied or true, the method proceeds to 914. At 914, the method determines whether it is the end of the cleaning cycle. In this regard, the method determines whether user input data 720 has been received to end the cleaning cycle. If true, the method ends at 918. The method may also determine the dosage data 378 for the liquid dispensed, and output the dosage data 378 to the other entities 180 and/or the display 184. Otherwise, if false at 914, the method loops to 910.

Thus, the mobile sanitization system 100, 600 enables cleaning of the surfaces of the mobile platform 102 that are both within a line of sight of the light sources 190 and outside of the line of sight through the use of the trolley nozzles 176 and the arm nozzles 192. Moreover, the spray wand 178 enables the operator to clean hard to access surfaces, including, but not limited to, stowage compartment handles, seatbelt buckles, corners of galleys and corners of lavatories. Thus, the mobile sanitization system 100, 600 provides for sanitization or disinfection of all surfaces associated with an interior of a mobile platform 102, which ensures cleanliness to a passenger onboard the mobile platform 102. In addition, due to the spray wand 178, in certain instances, the mobile sanitization system 100, 600 may complete the cleaning of the aisle 106 in a single pass or trip down the aisle 106, which may reduce an amount of time needed to clean the mobile platform 102. In one embodiment, the trolley nozzles 176 are used to effect disinfection of the floor or surfaces in the center aisle 106 or stowage compartments 108, while the surfaces of, on, and between the passenger seats 104 are cleaned by the light sources 190 on the arms 122a, 122b. Thus, in certain embodiments, the trolley 120 need not include the arm nozzles 192.

It should be noted that while the mobile sanitization system 100, 600 is described herein as adjusting the output of the light sources 190 based on the proximity of the surfaces of the arms 122a, 122b to a surface within the mobile platform 102, in other embodiments, the mobile sanitization system 100, 600 may be configured to adjust the position of the arms 122a, 122b based on the sensor signals from the arm proximity sensors 195. For example, based on the sensor signals from the arm proximity sensors 195, the controller 138, 638 may determine whether a distance between the surface within the mobile platform 102 and the respective surface of the respective arm 122a, 122b is within a threshold, and output actuator data to move the respective arm 122a, 122b relative to the surface so that the distance between the respective surface of the respective arm 122a, 122b and the surface within the mobile platform 102 is within the threshold.

In addition, it should be noted that while the controller 138, 638 is described herein as adjusting the light output (the light adjustment data 344) and the flow rate (pump adjustment data 340) based on the speed of the trolley 120, 620, the mobile sanitization system 100, 600 may be configured differently. In this regard, in certain embodiments, the light output of the light sources 190 and the flow rate of the pump 172 may be fixed. In this example, based on the speed data 374, the dosage manager module 316, 716 compares the speed data 374 to a predetermined, default or factory set speed for the trolley 120, 620. If the speed data 374 is greater than the predetermined, default or factory set speed, the dosage manager module 316, 716 sets a notification to the UI manager module 302, 702 to generate and output the user interface data 330 that renders a user interface that includes a warning that the trolley 120, 620 is moving too fast to ensure the mobile platform 102 is properly sanitized. Conversely, if the speed data 374 is less than the predetermined, default or factory set speed, the dosage manager module 316, 716 sets a notification to the UI manager module 302, 702 to generate and output the user interface data 330 that renders a user interface that includes a warning that the trolley 120, 620 is moving too slow to ensure the mobile platform 102 is properly sanitized.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

What is claimed is:

1. A mobile sanitization system, comprising:
   a movable trolley having an arm that is extendable from a first position in which the arm is in a collapsed state within the trolley and a second position in which the arm is extended outwardly from the trolley;
   at least one ultraviolet light source coupled to the arm, the at least one ultraviolet light source configured to illuminate to disinfect at least one surface;
   at least one source of a liquid disinfectant coupled to the trolley;
   at least one nozzle fluidly coupled to the at least one source of the liquid disinfectant, the at least one nozzle coupled to at least one of the trolley and the arm, the at least one nozzle configured to dispense the liquid disinfectant to disinfect the at least one surface;
   a valve coupled between the at least one source of the liquid disinfectant and the at least one nozzle, the valve responsive to one or more control signals to move between an opened position to enable the liquid disinfectant to flow to the at least one nozzle and a closed position;
   a spray wand removably coupled to the trolley and fluidly coupled to the at least one source of the liquid disinfectant, the spray wand configured to be removed from the trolley to dispense the liquid disinfectant to disinfect a targeted area of the at least one surface;
a propulsion system configured to move the trolley; and
a controller, having a processor, configured to:
output one or more control signals to the valve to move the valve to the opened position or the closed position based on a condition associated with the mobile sanitization system;
receive interlock data from an interlock sensor and determine whether the condition is satisfied based on the interlock data; and
based on the interlock condition as unsatisfied, output one or more control signals to the propulsion system to halt a movement of the trolley.

2. The mobile sanitization system of claim 1, wherein the trolley has a first end opposite a second end, the arm is coupled proximate the first end, and the at least one nozzle is coupled to the trolley proximate the second end.

3. The mobile sanitization system of claim 1, wherein the at least one nozzle comprises at least one nozzle coupled to each of the trolley and to the arm, and the valve is coupled between the at least one source of the liquid disinfectant and the at least one nozzle coupled to each of the trolley and to the arm.

4. The mobile sanitization system of claim 1, wherein the controller is configured to output the one or more control signals to the valve to move the valve to the opened position based on the interlock condition being satisfied.

5. The mobile sanitization system of claim 3, further comprising a source of speed data associated with a speed of the movement of the trolley, wherein the at least one ultraviolet light source is configured to illuminate based on the speed data.

6. The mobile sanitization system of claim 3, wherein the at least one ultraviolet light source is responsive to one or more control signals from the controller to illuminate, and the controller is configured to output the one or more control signals based on whether the spray wand is removed from the trolley.

7. The mobile sanitization system of claim 3, further comprising a communication system, wherein the controller is configured to determine an amount of liquid disinfectant dispensed by the at least one nozzle coupled to each of the trolley and to the arm and to output a dosage to a remote entity via the communication system.

8. The mobile sanitization system of claim 3, further comprising a source of speed data associated with a speed of the movement of the trolley and a pump configured to supply the at least one nozzle with the liquid disinfectant, wherein a flow rate of the pump is based on the speed data.

9. The mobile sanitization system of claim 1, wherein the trolley includes at least one handle, and the interlock sensor is associated with the at least one handle.

10. A mobile sanitization system, comprising:
a movable trolley having an arm that is extendable from a first position in which the arm is in a collapsed state within the trolley and a second position in which the arm is extended outwardly from the trolley;
at least one ultraviolet light source coupled to the arm, the at least one ultraviolet light source configured to illuminate to disinfect at least one surface;
at least one source of a liquid disinfectant coupled to the trolley;
at least one trolley nozzle fluidly coupled to the at least one source of the liquid disinfectant and coupled to the trolley, the at least one trolley nozzle configured to dispense the liquid disinfectant to disinfect the at least one surface;
at least one arm nozzle fluidly coupled to the at least one source of the liquid disinfectant and coupled to the arm, the at least one arm nozzle configured to dispense the liquid disinfectant to disinfect the at least one surface;
a spray wand removably coupled to the trolley and fluidly coupled to the at least one source of the liquid disinfectant, the spray wand configured to be removed from the trolley to dispense the liquid disinfectant to disinfect a targeted area of the at least one surface a propulsion system configured to move the trolley; and
a controller, having a processor, configured to:
receive interlock data from an interlock sensor and determine whether a condition is satisfied based on the interlock data; and
based on the interlock condition as unsatisfied, output one or more control signals to the propulsion system to halt a movement of the trolley.

11. The mobile sanitization system of claim 10, wherein the trolley has a first end opposite a second end, the arm is coupled proximate the first end, and the at least one trolley nozzle is coupled to the trolley proximate the second end.

12. Mobile sanitization system of claim 10, wherein the at least one arm nozzle comprises a plurality of arm nozzles coupled to the arm to extend about at least a portion of a perimeter of the arm.

13. The mobile sanitization system of claim 10, wherein the trolley includes at least one handle, and the interlock sensor is associated with the at least one handle.

14. A method of sanitizing one or more surfaces of a mobile platform, comprising:
receiving, by a processor of a controller, at least one of an input to activate at least one ultraviolet light source associated with a mobile sanitization system to illuminate to disinfect the one or more surfaces or an input to activate at least one trolley nozzle and at least one arm nozzle to dispense a liquid disinfectant associated with the mobile sanitization system to disinfect the one or more surfaces, the mobile sanitization system including a movable trolley having an arm that is extendable from a first position in which the arm is in a collapsed state within the trolley and a second position in which the arm is extended outwardly from the trolley, the at least one ultraviolet light source coupled to the arm, at least one source of liquid disinfectant coupled to the trolley, the at least one trolley nozzle fluidly coupled to the at least one source of liquid disinfectant and coupled to the trolley, the at least one arm nozzle fluidly coupled to the at least one source of liquid disinfectant and coupled to the arm, and the mobile sanitization system includes a spray wand removably coupled to the trolley and fluidly coupled to the at least one source of liquid disinfectant, the spray wand configured to be removed from the trolley to dispense the liquid disinfectant to disinfect a targeted area of the one or more surfaces, and a propulsion system configured to move the trolley;
determining, by the processer, whether an interlock condition associated with the mobile sanitization system is satisfied based on interlock data from an interlock sensor;
outputting, by the processor, one or more control signals to activate at least one of the at least one ultraviolet light source, the at least one trolley nozzle and the at least one arm nozzle based on the input and the interlock condition as satisfied;

deactivating, by the processor, the at least one ultraviolet light source, the at least one trolley nozzle or the at least one arm nozzle based on the input and the interlock condition as unsatisfied; and outputting one or more control signals to the propulsion system to halt a movement of the trolley based on the interlock condition as unsatisfied.

15. The method of claim 14, wherein deactivating the at least one trolley nozzle and the at least one arm nozzle further comprises:

outputting, by the processor, one or more control signals to a valve coupled between the at least one trolley nozzle, the at least one arm nozzle, and a reservoir to close the valve based on the interlock condition as unsatisfied.

16. The method of claim 14, further comprising:

determining, by the processor, whether an input has been received to dispense the liquid disinfectant through the spray wand associated with the mobile sanitization system based on the interlock condition.

17. The method of claim 14, wherein the input is to activate the at least one ultraviolet light source and the method further comprises:

receiving, by the processor, speed data associated with a speed of the mobile sanitization system;

determining, by the processor, whether a dosage of the at least one ultraviolet light source meets a guideline for the mobile platform based on the speed of the mobile sanitization system; and adjusting the output of the at least one ultraviolet light source based on the determining.

18. The method of claim 14, wherein the input is to activate the at least one trolley nozzle and the at least one arm nozzle, and the method further comprises:

receiving, by the processor, speed data associated with a speed of the mobile sanitization system;

determining, by the processor, whether a dosage of the at least one trolley nozzle and the at least one arm nozzle meets a guideline for the mobile platform based on the speed of the mobile sanitization system; and adjusting the output of the at least one trolley nozzle and the at least one arm nozzle based on the determining.

\* \* \* \* \*

UNITED STATES PATENT AND TRADEMARK OFFICE
CERTIFICATE OF CORRECTION

PATENT NO. : 11,844,872 B2
APPLICATION NO. : 17/150706
DATED : December 19, 2023
INVENTOR(S) : Peter Michalakos et al.

It is certified that error appears in the above-identified patent and that said Letters Patent is hereby corrected as shown below:

In the Claims

Column 42, Line 12 (Claim 10), after "surface" insert -- ; --

Signed and Sealed this
Sixteenth Day of April, 2024

Katherine Kelly Vidal
*Director of the United States Patent and Trademark Office*